US012765997B2

(12) United States Patent
Iyer et al.

(10) Patent No.: US 12,765,997 B2
(45) Date of Patent: Oct. 20, 2026

(54) EXPANDABLE FRAME FOR IMPROVED HEMODYNAMIC PERFORMANCE OF TRANSCATHETER REPLACEMENT HEART VALVE

(71) Applicant: Anteris Technologies Corporation, Eagan, MN (US)

(72) Inventors: Ramji Iyer, Plymouth, MN (US); David Lawrence St. Denis, Jr., Parkland, FL (US); Samuel Thomas Johnson, Plymouth, MN (US); William Morris Leonard Neethling, Booragoon (AU); Martha Jeanne Engel, Saint Paul, MN (US)

(73) Assignee: Anteris Technologies Corporation, Eagan, MN (US)

( * ) Notice: Subject to any disclaimer, the term of this patent is extended or adjusted under 35 U.S.C. 154(b) by 635 days.

(21) Appl. No.: 18/014,886

(22) PCT Filed: Jul. 7, 2021

(86) PCT No.: PCT/US2021/040592
§ 371 (c)(1),
(2) Date: Jan. 6, 2023

(87) PCT Pub. No.: WO2022/010954
PCT Pub. Date: Jan. 13, 2022

(65) Prior Publication Data

US 2023/0248513 A1 Aug. 10, 2023

Related U.S. Application Data

(60) Provisional application No. 63/070,857, filed on Aug. 27, 2020, provisional application No. 63/048,690, filed on Jul. 7, 2020.

(51) Int. Cl.
*A61F 2/24* (2006.01)

(52) U.S. Cl.
CPC .... *A61F 2/2418* (2013.01); *A61F 2210/0004* (2013.01); *A61F 2220/0008* (2013.01);
(Continued)

(58) Field of Classification Search
CPC ........ A61F 2/24; A61F 2/2418; A61F 2/2412; A61F 2/2415; A61F 2/2427;
(Continued)

(56) References Cited

U.S. PATENT DOCUMENTS 4,624,822 A 11/1986 Arru et al.
5,855,601 A 1/1999 Bessler et al.
(Continued)

FOREIGN PATENT DOCUMENTS

CN 103228232 A 7/2013
CN 103370034 A 10/2013
(Continued)

OTHER PUBLICATIONS

Office Action in Canadian Appln. No. 3,184,933, dated May 3, 2024, 5 pages.
(Continued)

*Primary Examiner* — Seema Mathew
(74) *Attorney, Agent, or Firm* — Fish & Richardson P.C.

(57) ABSTRACT

A replacement heart valve prosthesis for transcatheter repair of a native valve, the replacement heart valve comprises a valve construct mounted to the exterior surface of an expandable frame. The frame comprises an expandable region near the distal end of the frame, and a cusp region near the proximal region comprising a plurality of valve attachment features. The valve construct may be attached to the valve construct at least at the valve attachment features. The replacement heart valve prosthesis of present disclosure
(Continued)

may be a more durable and long-lasting valve that has added benefits by placing valve tissue between the expandable frame and native cardiac tissue.

20 Claims, 24 Drawing Sheets

(52) U.S. Cl.
CPC ................. *A61F 2220/0033* (2013.01); *A61F 2230/0013* (2013.01); *A61F 2250/001* (2013.01); *A61F 2250/0069* (2013.01); *A61F 2250/0098* (2013.01)

(58) Field of Classification Search
CPC .............. A61F 2240/001; A61F 2/2409; A61F 2/2475; A61F 2210/0076; A61F 2/86; A61F 2/2454; A61F 2002/072
See application file for complete search history.

(56) References Cited

U.S. PATENT DOCUMENTS 6,425,916 B1 * 7/2002 Garrison ............... A61F 2/2436 623/2.11
6,454,799 B1 * 9/2002 Schreck ................ A61F 2/2433 623/2.14
6,491,511 B1 12/2002 Duran et al.
6,682,559 B2 1/2004 Myers et al.
7,025,780 B2 4/2006 Gabbay
7,087,079 B2 8/2006 Navia et al.
8,052,750 B2 * 11/2011 Tuval .................... A61F 2/2436 623/2.14
8,398,704 B2 * 3/2013 Straubinger .......... A61F 2/2418 623/1.15
8,465,540 B2 * 6/2013 Straubinger .............. A61F 2/07 623/1.24
8,540,768 B2 9/2013 Stacchino et al.
8,709,077 B2 * 4/2014 Schreck ................ A61F 2/2469 623/2.14
8,778,018 B2 7/2014 Iobbi
8,808,366 B2 8/2014 Braido et al.
8,992,599 B2 3/2015 Thubrikar et al.
9,011,525 B2 4/2015 Claiborne, III et al.
9,095,430 B2 8/2015 Cunanan et al.
9,192,470 B2 11/2015 Cai et al.
9,205,172 B2 12/2015 Leonard Neethling et al.
9,259,313 B2 2/2016 Wheatley
9,301,835 B2 4/2016 Campbell et al.
9,326,856 B2 * 5/2016 Schraut ................. A61F 2/2445
9,345,571 B1 * 5/2016 Braido .................. A61F 2/2418
9,370,418 B2 * 6/2016 Pintor ................... A61F 2/2418
9,522,062 B2 * 12/2016 Tuval .................... A61F 2/2409
9,554,902 B2 1/2017 Braido et al.
9,622,863 B2 * 4/2017 Karapetian ............. A61F 2/246
9,744,037 B2 8/2017 Kheradvar et al.
9,763,780 B2 9/2017 Morriss et al.
9,974,651 B2 5/2018 Hariton et al.
10,201,416 B2 * 2/2019 Backus ................. A61F 2/2436
10,201,418 B2 * 2/2019 Biadillah .............. A61F 2/2418
10,575,944 B2 * 3/2020 Saar ...................... A61F 2/2418
11,135,059 B2 10/2021 Hammer et al.
11,185,405 B2 * 11/2021 Girard ................... A61F 2/2412
11,207,178 B2 * 12/2021 Conklin .................... A61F 2/24
11,337,800 B2 * 5/2022 Schreck ................ A61F 2/2418
11,464,635 B2 10/2022 Reimer et al.
11,622,853 B1 * 4/2023 Quill ..................... A61F 2/2418 623/2.12
11,806,233 B2 * 11/2023 Clapp ................... A61F 2/2436
12,011,349 B2 * 6/2024 Peterson ............... A61F 2/9522
12,329,635 B2 * 6/2025 Salahieh ............... A61F 2/2418
2003/0069635 A1 4/2003 Cartledge et al.
2005/0123582 A1 6/2005 Sung et al.
2005/0137687 A1 6/2005 Salahieh et al.
2005/0203614 A1 9/2005 Forster et al.
2005/0240262 A1 10/2005 White
2006/0020327 A1 1/2006 Lashinski et al.
2006/0025857 A1 * 2/2006 Bergheim ............... A61L 27/50 623/2.18
2008/0288055 A1 11/2008 Paul, Jr.
2009/0319037 A1 * 12/2009 Rowe .................... A61F 2/2427 623/2.11
2010/0049313 A1 2/2010 Alon et al.
2010/0262231 A1 * 10/2010 Tuval .................... A61F 2/2409 623/2.4
2010/0268332 A1 * 10/2010 Tuval .................... A61F 2/2436 623/2.1
2011/0066224 A1 3/2011 White
2011/0238167 A1 9/2011 Dove et al.
2012/0078356 A1 3/2012 Fish et al.
2012/0277855 A1 11/2012 Lashinski et al.
2013/0018458 A1 1/2013 Yohanan et al.
2013/0150956 A1 * 6/2013 Yohanan ............... A61F 2/2433 623/2.14
2013/0184811 A1 7/2013 Rowe et al.
2013/0197631 A1 8/2013 Bruchman et al.
2013/0204360 A1 8/2013 Gainor
2013/0310927 A1 11/2013 Quintessenza
2014/0005772 A1 1/2014 Edelman et al.
2014/0031924 A1 1/2014 Bruchman et al.
2014/0107772 A1 4/2014 Li et al.
2014/0180393 A1 6/2014 Roeder
2014/0188219 A1 7/2014 Conklin et al.
2014/0249622 A1 9/2014 Carmi et al.
2014/0277389 A1 9/2014 Braido et al.
2014/0277417 A1 9/2014 Schraut et al.
2014/0324160 A1 10/2014 Benichou et al.
2014/0343671 A1 * 11/2014 Yohanan ............... A61F 2/2418 623/2.18
2015/0018944 A1 * 1/2015 O'Connell ............ A61F 2/2427 623/2.42
2015/0134056 A1 5/2015 Claiborne, III et al.
2015/0142104 A1 5/2015 Braido
2015/0209141 A1 7/2015 Braido et al.
2015/0216663 A1 8/2015 Braido et al.
2015/0230923 A1 8/2015 Levi
2015/0289973 A1 10/2015 Braido et al.
2015/0320556 A1 11/2015 Levi et al.
2016/0128831 A1 5/2016 Zhou et al.
2016/0135951 A1 5/2016 Salahieh et al.
2016/0143732 A1 5/2016 Glimsdale
2016/0158007 A1 6/2016 Centola et al.
2016/0175095 A1 6/2016 Dienno et al.
2016/0213465 A1 * 7/2016 Girard ................... A61F 2/2418
2016/0220365 A1 8/2016 Backus et al.
2016/0317293 A1 11/2016 Matheny et al.
2016/0331532 A1 11/2016 Quadri
2016/0367360 A1 12/2016 Cartledge et al.
2016/0367364 A1 12/2016 Torrianni et al.
2017/0049566 A1 2/2017 Zeng et al.
2017/0056170 A1 3/2017 Zhu et al.
2017/0119525 A1 5/2017 Rowe et al.
2017/0189174 A1 7/2017 Braido et al.
2017/0258585 A1 9/2017 Marquez et al.
2017/0312075 A1 11/2017 Fahim et al.
2018/0028312 A1 2/2018 Thill et al.
2018/0228603 A1 8/2018 Racchini et al.
2019/0117390 A1 4/2019 Neethling et al.
2020/0188099 A1 6/2020 Dvorsky et al.
2020/0246141 A1 * 8/2020 Peterson ............... A61F 2/2433
2021/0212819 A1 7/2021 Reed et al.
2021/0212822 A1 7/2021 Reed et al.
2021/0212823 A1 7/2021 Reed et al.
2021/0275298 A1 9/2021 Peterson et al.
2022/0211494 A1 * 7/2022 Benichou .............. A61F 2/2412
2022/0211498 A1 * 7/2022 Benichou .............. A61F 2/2418
2024/0081984 A1 * 3/2024 Peterson ............... A61F 2/2418

(56) References Cited

U.S. PATENT DOCUMENTS

| | | | | |
|---|---|---|---|---|
| 2024/0293227 | A1* | 9/2024 | Kuske | A61F 2/2418 |
| 2025/0325363 | A1* | 10/2025 | Lo | A61F 2/2433 |

FOREIGN PATENT DOCUMENTS

| | | | |
|---|---|---|---|
| CN | 203736349 | | 7/2014 |
| CN | 105555232 | A | 5/2016 |
| CN | 105792780 | A | 7/2016 |
| CN | 107233146 | A | 10/2017 |
| CN | 107920894 | A | 4/2018 |
| CN | 110025405 | A | 7/2019 |
| CN | 111148486 | A | 5/2020 |
| CN | 111265338 | A | 6/2020 |
| EP | 2777618 | | 9/2014 |
| EP | 2967869 | | 1/2016 |
| EP | 3697343 | | 8/2020 |
| JP | 2008-264553 | | 11/2008 |
| JP | 2013-543397 | A | 12/2013 |
| JP | 2015-519187 | | 7/2015 |
| JP | 2016-107078 | A | 6/2016 |
| JP | 2017-505705 | A | 2/2017 |
| KR | 20110126517 | | 11/2011 |
| WO | 2001076510 | | 10/2001 |
| WO | 2003030776 | | 4/2003 |
| WO | 2007013999 | | 2/2007 |
| WO | WO 2009149462 | A2 | 12/2009 |
| WO | WO 2010141847 | | 12/2010 |
| WO | 2011072084 | | 6/2011 |
| WO | 2011109450 | | 9/2011 |
| WO | WO 2014164832 | | 10/2014 |
| WO | 2014204807 | | 12/2014 |
| WO | 2015126712 | | 8/2015 |
| WO | 2015173794 | | 11/2015 |
| WO | 2017031155 | | 2/2017 |
| WO | WO 2019078979 | | 4/2019 |
| WO | 2019144036 | | 7/2019 |
| WO | WO 2022010958 | | 1/2022 |
| WO | WO 2022010958 | A1 | 1/2022 |

OTHER PUBLICATIONS

Ariki et al., "Doppler echocardiographic assessment of the aortic prosthetic valves by means of the continuity equation," Artificial Organs, Japan, 1993, 22(3): 785-788 (with English Abstract).

Knee Hiang Lim et al., Flat or Curved Pericardial Aortic Valve Cusps: A Finite Element Study, Journal of Heart Valve, vol. 13, No. 5 (Sep. 2004).

Search Report and Written Opinion for related PCT Application No. PCT/US2021/040592 mailed Oct. 26, 2021 (9 pages).

Search Report and Written Opinion for related PCT Application No. PCT/US2021/040596 mailed Oct. 26, 2021 (9 pages).

Extended European Search Report in European Appln No. 21836892.6, dated Jul. 23, 2024, 11 pages.

AU Notice of Acceptance in Australian Appln. No. 2021303413, dated May 8, 2023, 3 pages.

* cited by examiner

EXPANDABLE FRAME FOR IMPROVED HEMODYNAMIC PERFORMANCE OF TRANSCATHETER REPLACEMENT HEART VALVE

CROSS-REFERENCE TO RELATED APPLICATIONS

The present disclosure is a US National Stage Application of PCT/US21/40592, filed Jul. 7, 2021, which claims priority to U.S. Provisional Application No. 63/048,690, filed Jul. 7, 2020, and to U.S. Provisional Application No. 63/070,857 filed Aug. 27, 2020, the contents of which are hereby incorporated by reference herein in their entirety.

BACKGROUND OF THE INVENTION

The present disclosure relates to novel and advantageous expandable frames for use with a transcatheter replacement heart valve prosthesis, and methods for attaching a valve construct to the frame.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Transcatheter valve replacement (TVR) is a minimally invasive heart procedure to repair or replace a valve of the heart by using an implantable valve prosthesis delivered to the patient's native valve via a catheter. The implantable valve prosthesis typically comprises an expandable frame with multiple flat prosthetic leaflets attached to the interior of the expandable frame. The prosthetic leaflets are intended to mimic the action of healthier native leaflets. The expandable frame may either be self-expanding using a shape memory alloy or may be expandable with a balloon or otherwise mechanically expandable when deployed into the native valve. Transcatheter valve replacement prostheses have been developed for the aortic, mitral, and tricuspid valves. TVR procedures typically involve the introduction of a catheter to the patient's vasculature transfemorally, where the valve prosthesis is loaded into the catheter and advanced through the patient's vasculature to the native valve.

Before these minimally invasive transcatheter valve replacement procedures were developed, the options for most patients needing to their heart valve repaired were limited to significantly invasive surgical replacement procedures. Yet for many patients needing heart valve repair, surgical repair posed a relatively high risk or the patient was not a viable candidate for surgery. With respect to the aortic valve, transcatheter aortic valve replacement (TAVR) procedures have been widely adopted by clinicians throughout the world as an alternative to surgical replacement procedures to treat these high-risk patients having severe aortic stenosis or similar conditions. With many procedures over the decades, TAVR has been shown to improve long term survival of these patients. Additionally, in recent years, several studies involving both balloon-expandable and self-expanding TAVR prostheses demonstrated that TAVR procedures showed effectiveness for patients with low surgical risk, and in 2019, the U.S. Food & Drug Administration expanded the TAVR indication to include these low-risk patients.

The development of TAVR prostheses, and the related prior art, has focused significantly on the mechanisms and methods for delivering the prosthesis to the native valve, positioning or re-positioning the prosthesis relative to the native valve structure or surrounding anatomical structure, and reducing the French size of the catheter for improvement of delivery through the vascular. However, this development has not focused especially on long-term use and hemodynamic performance of the prostheses over time. Many of the TAVR prostheses currently used in these procedures have shown significant calcification, as well as deterioration or degradation of the prosthesis. Over time, typically between five and fifteen years, many TAVR valve prostheses degenerate and eventually fail, requiring the patient to then have the valve prostheses repaired. In recent years, a second valve may be provided to a patient with a failed TAVR prostheses in a procedure called "valve-in-valve" TAVR. In these procedures, a new transcatheter valve is inserted into the lumen of the failed TAVR valve, pushing the prosthetic leaflets aside. Inserting a valve into the lumen of the failed TAVR valve, necessarily restricts or reduces the effective orifice area, and thus limits the hemodynamic performance of this second valve.

As younger, lower-risk patients receive TAVR prostheses, there is a need for a more durable valve that effectively resists calcification and degradation of the prosthesis. Further, there is a need in the art for a durable heart valve that also achieves improved hemodynamic performance, in addition to its longevity.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure relates to novel and advantageous frames for a valve prosthesis that minimize wear on the valve construct attached to the frame, while maximizing the effective orifice area of the prosthesis. The effective orifice area of the valve is an important metric in measuring hemodynamic performance of the valve.

In some embodiments, as described in the present disclosure, a valve construct comprising at least one leaflet may be mounted onto the exterior surface of the frame. Prior art valves typically have prosthetic leaflets mounted instead to the interior surface of the frame, within the lumen of the frame. For these prior art valves, when they are deployed in the native valve, the metal alloy frame abuts the native cardiac tissue of the patient, which can contribute to inflammation in the area, calcification of the prosthesis, and performance issues for the valve prosthesis such as paravalvular leak. By instead mounting the valve construct to the exterior of the valve, the metal alloy frame may no longer abut the native cardiac tissue of the patient, and inflammation from the frame may be reduced. The interior surface of the frame may define a lumen, and the frame may be designed to allow cusps or leaflets of the valve construct to coapt in the center of the lumen of the frame to close the valve. Certainly, in other embodiments of the invention described herein, the valve construct may be mounted onto the interior surface of a frame of the present disclosure.

In at least one embodiment, a replacement heart valve prosthesis for transcatheter repair of a native valve, the replacement heart valve comprises a frame and a valve construct. The frame has a distal end, a proximal end, and a length between the distal end and the proximal end. The frame further comprising an exterior surface and an interior surface defining a lumen. The frame is expandable from an unexpanded state to an expanded state. The frame further comprises an expandable region near the distal end of the frame; and a cusp region near the proximal region comprising a plurality of valve attachment features. The valve construct mounted to the exterior surface of the frame, wherein the valve construct is attached to the valve construct at least at the valve attachment features. In some embodiments, the cusp region comprises a plurality of posts. In at least one embodiment, the post is connected to a circumferentially adjacent post with a strut, the strut defining a cusp opening. The valve construct may comprise at least two leaflets. Each leaflet may span an adjacent cusp opening and then the leaflet traverses the cusp opening into the lumen of the frame. In at least one embodiment, the strut is an arched strut.

In at least one embodiment of the present disclosure, a replacement heart valve prosthesis for transcatheter repair of a native valve comprises a frame and a valve construct attached to the frame, the valve construct comprising at least one leaflet. The frame may have an exterior surface and an interior surface defining a lumen. In some embodiments, the valve construct is externally mounted onto the frame such that the interior surface of the valve abuts the external surface of the frame. In other embodiments, the valve construct is internally mounted onto the frame such that the exterior surface of the valve construct abuts the internal surface of the frame. The frame may be expandable from an unexpanded state to an expanded state. The frame may have a distal end, a proximal end, and a length between the distal end and the proximal end. The frame may have an expandable region defining the distal end of the frame and extending towards the proximal end of the frame and a plurality of valve posts extending proximally from the expandable region. The expandable region may have at least a first row of cells at a distal end, a second row of cells at a proximal end of the expandable region. In some embodiments, the expandable region may additionally have a plurality of middle row cells between the first row of cells and the second row of cells. Each valve post comprises a valve attachment feature, and the valve construct may be attached to the frame at least at the valve attachment features.

In some embodiments, each valve post has a proximal end and a distal end and a length therebetween, wherein the length of the valve post is between 25% and 75% of the length of the frame. In some embodiments, circumferentially adjacent valve posts are positioned equidistant from one another around a circumference of the frame. In some embodiments, the frame may have two valve posts. In other embodiments, the frame may have three valve posts. In still other embodiments, the frame may have more than three valve posts.

In some embodiments, the valve construct may comprise at least two shaped leaflets with a commissural region between the two shaped leaflets, and the commissural region of the valve construct is attached to the posts. In some embodiments, the valve construct comprises a single piece of biomaterial. In some embodiments, the valve construct comprises three leaflets shaped into the single piece of biomaterial. In some embodiments, the biomaterial comprises a polymer, bovine tissue, porcine tissue, or pericardium.

In some embodiments, the posts may further comprise commissural alignment markers. In at least one embodiment, the commissural alignment markers are radiopaque markers.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the disclosure will be better understood from the following description taken in conjunction with the accompanying Figures, in which:

DETAILED DESCRIPTION

The present disclosure describes novel and advantageous valve prosthesis with frames for mounting a valve construct, as well as methods for mounting the valve construct to the frame. While the embodiments and techniques discussed below may be discussed with respect to aortic valve replacement, it is within the scope of this disclosure that the inventions of the present disclosure may be suitable for use in other valve replacement, such as mitral and tricuspid valves. Further, while the figures and embodiments discussed below may describe an aortic valve that typically have three leaflets, it is within the scope of this disclosure that the inventions of the present disclosure may be suitable for prostheses for use in bicuspid aortic valves.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, and/or components have not been described in detail so as not to obscure the discussion.

In at least some embodiments of the present disclosure, a valve construct may be mounted to an expandable frame of the transcatheter valve prosthesis on an external surface of the frame, rather than the typical interior surface of the frame. In such embodiments, in the expanded state of the valve prosthesis, the valve construct may have a diameter that is larger than the diameter of the frame.

Figure 1A:
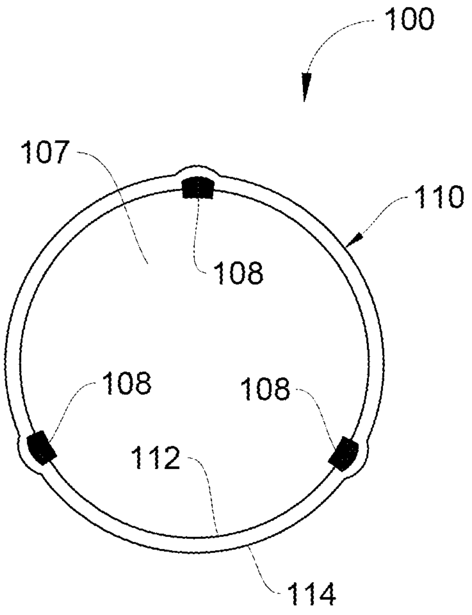
FIGS. 1A-1B show schematic diagrams of a valve prosthesis of the present invention with the valve construct mounted on the exterior of the frame in systolic and diastolic phases, respectively.
Figure 1B:
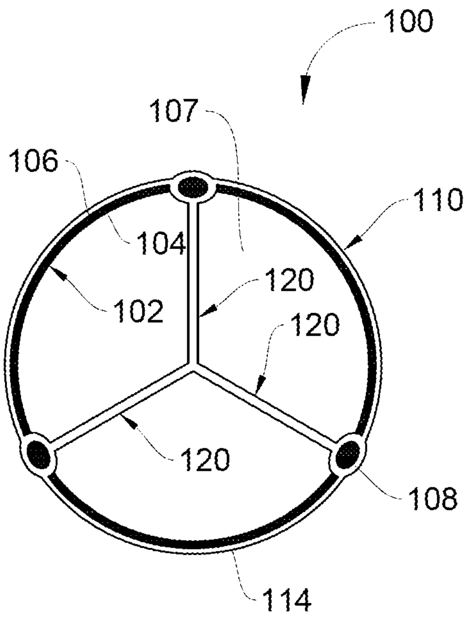

FIGS. 1A-1B show schematic diagrams of a valve prosthesis 100 of the present disclosure from one end of the prosthesis. The valve prosthesis 100 may be designed for either supra-annular placement or intra-annular placement. Valve prosthesis 100 comprises an expandable frame 102 having an interior surface 104 and an exterior surface 106. The interior surface 104 of the expandable frame 102 defines a lumen 107. In some embodiments, the expandable frame may comprise a plurality of posts 108. The valve prosthesis 100 further comprises a valve construct 110, which as shown in FIGS. 1A-1B is mounted to the exterior surface 106 of the expandable frame 102. The valve construct 110 may comprise a biomaterial, as discussed further below. The valve construct 110 may have an interior surface 112 and an exterior surface 114 with a thickness therebetween. As attached to the expandable frame 102, the interior surface 112 of the valve construct 110 abuts the exterior surface 106 of the expandable frame 102. The valve construct 110 may have at least one leaflet 120. In a preferred embodiment for the aortic valve, the valve construct 110 may have at least three leaflets 120. The leaflets 120 are able to fluctuate or move relative to the expandable frame 102 so as to allow the leaflets to coapt with one another during diastole without regurgitation and open fully to promote at least adequate blood flow and improved hemodynamics during systole. In at least some embodiments, the effective orifice area for the valve prosthesis 100 is between about 1.7 and 3.5 $cm^2$. In at least some embodiments, the mean effective orifice area for the valve prosthesis 100 is between about 2 and 3.5 $cm^2$. In at least some embodiments, the mean effective orifice area for the valve prosthesis 100 is between about 2.2 and 3.5 $cm^2$. In at least some embodiments, the mean effective orifice area for the valve prosthesis 100 is between about 2.5 and 3.5 $cm^2$. In at least one embodiment, the valve prosthesis 100 has a mean effective orifice area between about 2.5 and 3.5 $cm^2$ and a pressure gradient between about 4-7 mm Hg with a Doppler Velocity Index factor between 0.55 and 0.70. In at least one embodiment, the valve prosthesis 100 has a mean effective orifice area between about 2.5 and 3.5 $cm^2$ and a pressure gradient between about 4-10 mm Hg with a Doppler Velocity Index factor between 0.55 and 0.70. When deployed into the patient's native heart valve, the valve construct with the tissue mounted on the exterior frame may directly abuts the tissue of the native heart valve, whereas the typical valve prosthesis conversely has the valve construct mounted to the interior of the expandable frame on its exterior, so the metallic expandable frame abuts the tissue of the native heart valve which can promote inflammation. By having the valve construct 110 directly abut the tissue of the native heart valve, inflammation may be reduced. Additionally, by having the tissue on the exterior of the expandable frame, the valve prosthesis 100 may have a larger opening area, which can result in improved hemodynamics. Further, by having the tissue on the exterior of the expandable frame, the valve prosthesis 100 may have reduced gradients across the valve during forward flow, which can result in improved hemodynamics. Depending on the biomaterial used for the valve construct 110, the biomaterial may even remodel with the adjacent native heart valve tissue to affix the valve construct 110 to the native structure, which can prevent paravalvular leak and reduce the risk of migration of the valve prosthesis. In such examples where such material is used, the valve prosthesis of the present disclosure may eliminate any need for a polymer skirt, fabric skirt, or expandable material such as foam to prevent paravalvular leak, which are typically present in most commercial valve prostheses. In other examples, portions of the valve construct 110 may have a coating such as an adhesive to assist with affixation of the valve construct 110 to the native valve structure. Still other examples of the valve prosthesis of the present disclosure may include a polymer skirt, fabric skirt, or other paravalvular leak solution.

In some embodiments, the valve construct may further extend over at least a portion of both the interior and exterior surface of the posts 108. More particularly, a portion of the valve construct between the leaflets which may be described as the commissural region of the valve construct may align with the posts 108 and in some embodiments may be wrapped over the posts 108 so that the interior and exterior surface of the posts 108 are covered by the tissue material of the valve construct. In some embodiments, the valve construct may also be folded over the distal end (or annular end) of the expandable frame to form a cuff, such that the valve construct may be on both the interior surface and the exterior surface of the expandable frame at the distal end of the expandable frame.

In some embodiments, the expandable frame 102 may be a self-expanding frame and in other embodiments, the expandable frame 102 may be a balloon expandable or otherwise mechanically expandable frame. In still other embodiments, the expandable frame may have self-expanding regions and balloon-expandable regions. For example, the region of the frame near the leaflets may be self-expanding to control expansion of the leaflet area using a shape memory alloy, while the region of the frame nearest the annulus may be balloon-expandable to promote control of placement within the annulus. The expandable frame 102 may have a constant diameter from distal end to proximal end. The expandable frame 102 may have a greater diameter at the proximal end relative to the distal end, or conversely a greater diameter at the distal end relative to the proximal end, which effectively creates a taper of the valve. In some embodiments, the expandable frame 102 may have a flared shape from the distal end to the proximal end.

The expandable frame 102 may be constructed from stainless steel, shape memory alloys, plastically deformable alloys, or combinations thereof. Examples of such alloy materials include, but are not limited to, nickel-titanium alloys such as NITINOL® alloys, cobalt-chromium alloys such as ELGILOY® alloys, platinum-tungsten alloys, tantalum alloys, and so forth. Other alloys which may be employed in making the formation of the frame include, but are not limited to, other cobalt-chromium alloys, titanium cobalt-chromium molybdenum alloys, and so forth. In addition to these materials, the expandable frame 102 may further be constructed from polymers, biomaterials, or combinations thereof. In some embodiments, the expandable frame 102 may have a coating on at least a portion of one of either the exterior surface 106 or the interior surface 104. The coating may comprise a polymer, including but not limited to polytetrafluoroethylene (PTFE), silicone, biopolymers and other suitable polymers. In other embodiments, the coating may comprise a radiopaque material. In some embodiments, the coating may comprise a drug-eluting material.

The valve construct 110 may comprise a tissue material. In some embodiments, the tissue material may be a biomaterial. In some embodiments, the tissue material may be a cross-linked collagen-based biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of commonly owned U.S. Pat. No. 9,205,172, filed on Dec. 21, 2005 and entitled "Implantable Biomaterial and Method of Producing Same," which is incorporated by reference herein in its entirety. In some embodiments, the cross-linked collagen-based biomaterial is treated with the ADAPT® treatment process, which is an anti-calcification treatment process for biomaterials that leaves zero residual DNA and has over ten years of clinical data demonstrating no calcification when used in cardiac surgeries. In some embodiments, the tissue material may be artificial tissue. In some embodiments, the artificial tissue may comprise a single piece molded or formed polymer. In some embodiments, the artificial tissue may comprise polytetrafluoroethylene, polyethylene terephthalate, other polymers, and other polymer coatings. The valve construct 108 may, in some embodiments, comprise shaped tissue material. More particularly, at least some or all of the leaflets 120 of the valve construct 110 may comprise shaped tissue material. In some embodiments, the valve construct 110, including leaflets 120, is a single-piece three-dimensional valve construct constructed from a single piece of tissue material, such as the valve described in the disclosure of commonly owned U.S. application Ser. No. 16/129,235 and entitled "Replacement Heart Valve with Reduced Suturing," which is incorporated by reference herein in its entirety.

FIGS. 2-10 show various embodiments of an expandable frame of a valve prosthesis that provides improved hemodynamic performance of the valve prosthesis according to the invention of the present disclosure. Each expandable frame depicted in these figures and discussed further below may be constructed from the frame materials discussed above. Further, each expandable frame may be attached to a valve construct, which may be constructed as discussed above. In some embodiments, a valve construct is mounted to the exterior of the frame, and in other embodiments, the valve construct may be mounted to the interior of the frame.

Figure 2:
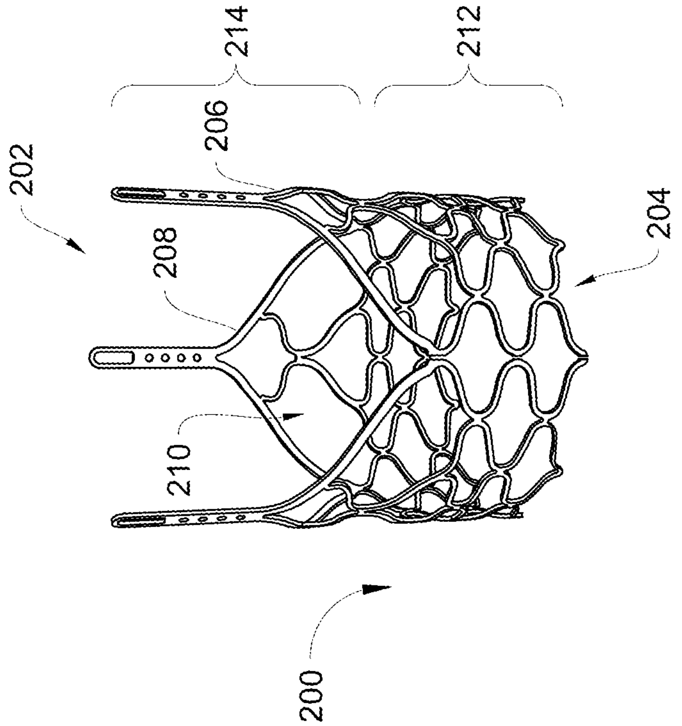
FIG. 2 is a perspective view of the expandable frame in an expanded state, in accordance with at least one embodiment of the present disclosure.
Figure 3:
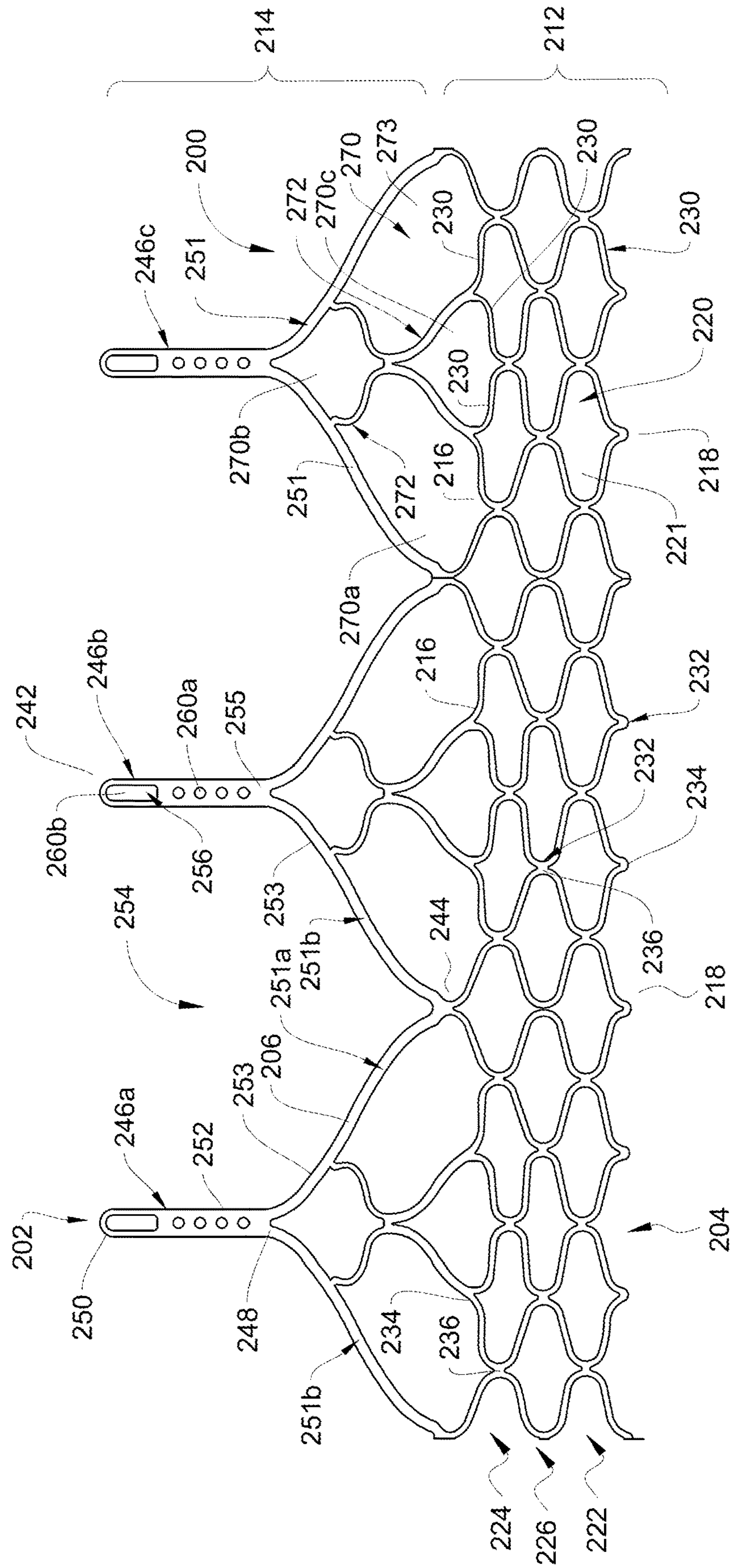
FIG. 3 is a flat, schematic diagram of the expandable frame shown in FIG. 2 in an expanded state.
Figure 4:
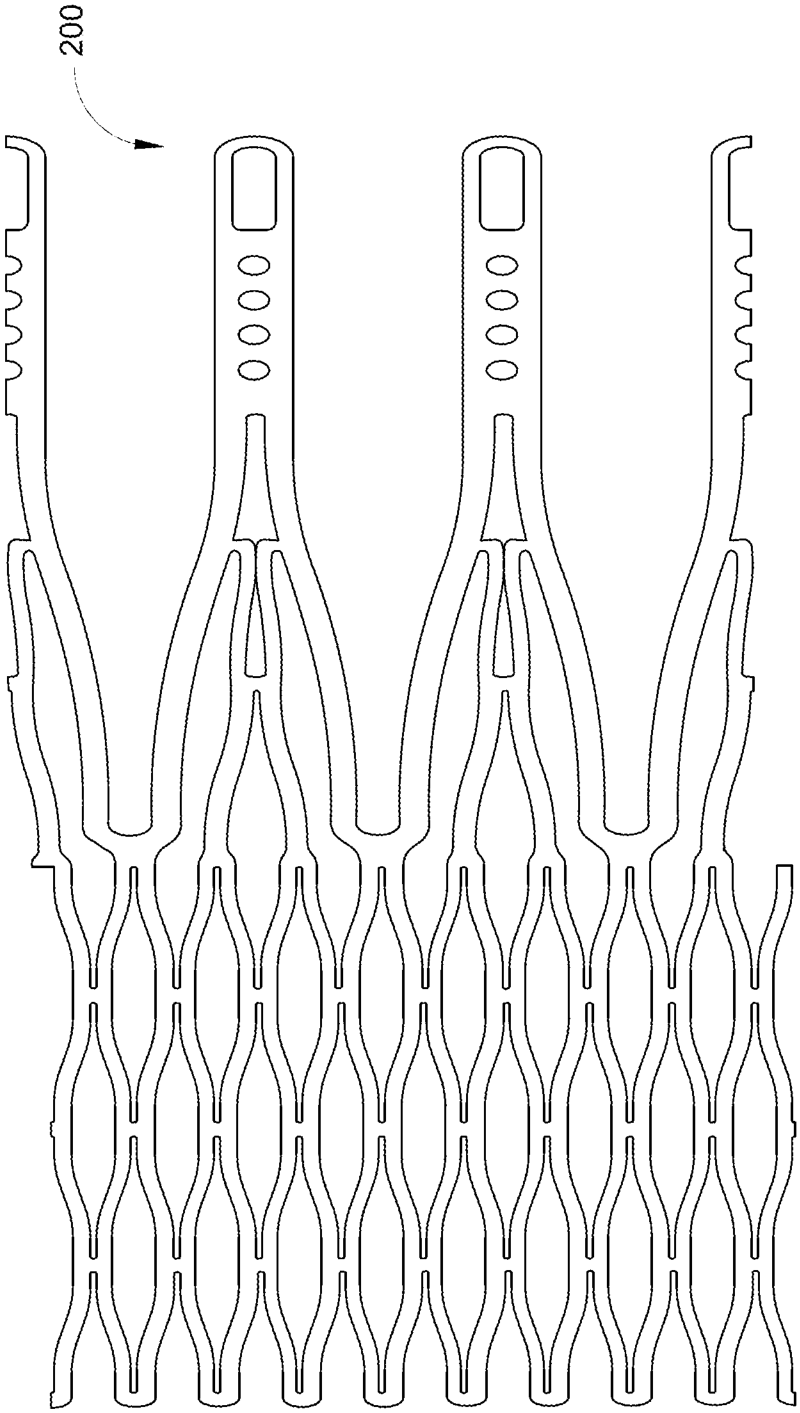
FIG. 4 is a flat, schematic diagram of the expandable frame shown in FIG. 2, in an unexpanded state.

FIGS. 2-4 show one embodiment of an expandable frame 200 for a prosthesis of the present disclosure. In some embodiments, a valve construct (not shown) is mounted to the exterior of the frame 200, and in other embodiments, the valve construct (not shown) may be mounted to the interior of the frame 200. FIG. 2 shows a perspective view of the expandable frame 200 in the expanded state. FIG. 3 shows a schematic diagram of the flat, stent pattern of the expandable frame 200 of FIG. 2 in the expanded state, while FIG. 4 shows a schematic diagram of the flat stent pattern of the expandable frame 200 of FIG. 8 in the unexpanded state.

Expandable frame 200 may have a proximal end 202 and a distal end 204 opposite the proximal end 202, with an axial length of the expandable frame spanning between the proximal end 202 and the distal end 204. The expandable frame 200 may have an exterior surface 206 and an interior surface 208 with a thickness therebetween. The interior surface 208 defines a lumen 210. Expandable frame 200 may have an expandable region 212 and a cusp region 214 proximal to the expandable region 212. The cusp region 214 allows for the leaflets of the valve construct to open beyond the exterior surface 206, and in some embodiments more particularly allow for the leaflets to open beyond the exterior surface 206 of at least the expandable region 212 of the expandable frame, which may be considered to be the ventricular section of the frame. This effectively may result in a tapered effect, where the area defined by a free edge of the leaflets of the valve construct is larger than the area defined by the exterior surface of the frame, resulting in reduced pressure gradients and increased effective orifice area during forward flow. Prior art valve prostheses do not allow the leaflets to open beyond the exterior surface of the expandable frame because of the frame's cell structure.

The expandable region 212 may be responsible for anchoring or sealing of the valve prosthesis. The expandable region 212 has a proximal end 216 and a distal end 218. The expandable region 212 comprises a plurality of cells 220 defining openings 221. In the embodiment shown in FIGS. 2-3, the openings 221 have different sizes and shapes. In other embodiments, the openings 221 may have the same sizes and shapes.

Cells 220 may be arranged into at least a first row of circumferentially adjacent cells, shown generally at 222, at a proximal end 216 of the expandable region 212 and a second row of circumferentially adjacent cells, shown generally at 224, at a distal end 218 of the expandable region 212. In some embodiments, such as the embodiments shown in FIGS. 2-4, at least one middle row of circumferentially adjacent cells, shown generally at 226, may span between the first circumferential row of cells 222 and the second circumferential row of cells 224.

Each cell 220 comprises a plurality of struts 230. Each strut 230 may be a straight strut or, as shown at least in FIGS. 2-4, may be a curved strut or each strut may be a serpentine strut with at least one turn or undulation. Each strut 230 may have a thickness that may be uniform or may vary over the length of the strut 230. Each strut of the cell 220 may be connected to an adjacent strut at a node 232. Nodes 232 may include end nodes 234 at the proximal end 216 and distal end 218 of the expandable region that connect circumferentially adjacent struts 230 at each end 216, 218. Nodes 232 may also include row nodes 236 that either connect circumferentially adjacent struts 230 in a row 222, 224, 226 or connect axially adjacent struts 230 of one row 222, 224, 226 to an axially adjacent row.

Turning now to the cusp region 214, which is intended to facilitate or assist with movement of the leaflets of a valve construct attached to the expandable frame 200, the cusp region 214 has a proximal end 242 and a distal end 244 adjacent the expandable region 212. The cusp region 214 comprises a plurality of posts 246 for attachment of the valve construct to the expandable frame 200. In some embodiments, the cusp region 214 may have two posts 246. In some embodiments, such as the embodiment shown in FIGS. 2-4, the cusp region 214 may have three posts 246. In still other embodiments, the cusp region 214 may have any number of posts 246.

Each post 246 may have a distal end 248 and a proximal end 250, where the proximal end 250 defines the proximal end 242 of the cusp region 242. In some embodiments, the distal end 248 of the post 246 may be attached to an end node 234 at the proximal end 216 of the expandable region 212. In other embodiments, the distal end 248 of the post 246 may be attached to an arched strut that spans the circumferential distance between circumferentially adjacent posts 246, and the arched strut may be attached to the expandable region at one or more end nodes 234. In still other embodiments, such as the embodiment shown in FIGS. 2-4, the distal end 248 of the post 246 may be attached to one or more cusp struts 251 of the cusp region 214, and each cusp strut may be attached to the expandable region 212 at one or more end nodes 234. As shown more particularly at least in FIG. 3, each post 246 may be connected to a right cusp strut **251*a* and a left cusp strut 251*b*. In at least the embodiment shown, the combination of the post 246, the right cusp strut 251*a* and the left cusp strut 251*b* creates a wishbone-like structure. In the embodiment shown, the right cusp strut 251*a* of a first post 246*a* and the left cusp strut 251*b* of a second post 246*b* (which is circumferentially adjacent to the first post 246*a*) are connected to the same end node 234 of the expandable region 212. The posts 246 each have a side surface 252 and the right cusp struts each have a side surface 253. The side surface 252 of the post 246*a*, the side surface 252 of the post 246*b*, the side surface 253 of the right cusp strut 251*a*, the side surface 253 of the left cusp strut 251*b* that is circumferentially adjacent the right cusp strut 251*b* define leaflet opening 254. The leaflet opening 254 allows the leaflets of the valve construct to traverse the exterior surface 206 of the expandable frame 200. The leaflet opening 254** may also allow for improved coronary access.

Each post 246 may comprise at least one strut 255, which may include at least one attachment feature 256 disposed within the strut 255. The strut 255 may have a width that is greater than a width of at least one strut 230 of the expandable region 214. In at least the embodiment shown in FIG. 3, the attachment feature 256 may comprise one or more openings 260. As shown in FIG. 3, the openings 260 may be holes **260*a* or one or more slots 260*b*. In still other embodiments, the attachment feature 256 may comprise a plurality of openings 260 that facilitate a specific suture pattern, said openings being comprised of holes, slots, or slits. In other embodiments, the at least one attachment feature may comprise hooks, loops, pledgets, or other attachment features. In some embodiments, the posts 246 and/or the attachment features 256 may further be utilized for recapturing or repositioning of the frame during or after deployment. In some embodiments, the posts 246, the attachment features 256, and/or one or more cusp struts 251** may be utilized for valve-in-valve procedures to either engage with a previously implanted valve prosthesis or to engage with a valve prosthesis being implanted.

The cusp region 214 may further comprise one or more cusp region cells 270, which may be defined by one or more cusp connector struts 272. The cusp connector struts 272 may provide some additional structure to the post 246 to handle stresses incurred by the cusp region as the valve pulsates between systolic and diastolic phases. The cusp connector struts 272 may have a width that is greater than a width of at least one strut 230 of the expandable region 214. As shown in FIGS. 2-3, the cusp region cells 270 have openings 273 that are larger than the openings 221 of cells 220. Some of the cusp region cells **270*a* may be defined, in some embodiments, by at least one cusp strut 251, at least one cusp connector strut 272, and one or more struts 230 at the proximal end 216 of the expandable region 212. Other cusp region cells 270*b* may be defined, in some embodiments, by at least two cusp struts 251 and two cusp connector struts 272. Still other cusp region cells 270*c* may be defined, in some embodiments, by at least two struts 230 of the proximal end 216 of the expandable region 212 and two cusp connector struts 272. Cusp region cells 270*a* may define an area larger than cusp region cells 270*b* and 270*c*, respectively. Cusp region cells 270*a* may have a different shape than cusp region cells 270*b* and 270*c*, respectively. In other embodiments, cusp region cells 270*a* may be smaller than cusp region cells 270*b* and 270*c*, respectively. In one embodiment, cusp region cells 270*b* may have substantially the same shape as cusp region cells 270*c*, and in one embodiment cusp region cells 270*b* may in some embodiments be the same size or slightly larger than cusp region cells 270*c*. In other embodiments, cusp region cells 270*b* may have substantially a different shape than cusp region cells 270*c*. In still other embodiments, cusp region cells 270*b* may be smaller than cusp region cells 270*c***.

In some embodiments, a diameter of the cusp region 214 may be greater than a diameter of the expandable region 212. In some embodiments, the diameter of the cusp region 214 at a proximal end of the cusp region 214 may be similar to the diameter of the expandable region 212 at the distal end of the expandable region 212. In some embodiments, the diameter of the cusp region 214 at a proximal end of the cusp region 214 may be greater than the diameter of the expandable region 212 at the distal end of the expandable region 212. In at least one embodiment, the diameter of the cusp region 214 may be greater at the proximal end of the cusp region than at the distal end of the cusp region, such that the cusp region 214 has a tapered profile in the expanded state.

In some embodiments, the axial length of the cusp region 214 in the expanded state shown in FIGS. 2-3 is between about 25% and 75% of the axial length of the expandable frame 200. In some embodiments, the axial length of the cusp region 214 in the expanded state shown in FIGS. 2-3 is between about 45% and 70% of the axial length of the expandable frame 200. In at least one embodiment, the axial length of the cusp region 814 in the expanded state shown in FIGS. 2-3 is between about 60% and 75% of the axial length of the expandable frame 200.

FIG. 4 shows the expandable frame 200 in an unexpanded state. As shown in FIG. 4, the end nodes 232 at the distal end 218 of the frame 200 are all radially aligned. As shown in FIG. 4, the row nodes 236 are also all radially aligned, as are the end nodes 232 at the proximal end 216 of the expandable frame 200. Unlike how the cells 220 of the expandable region 212 appear in their expanded state as shown in FIGS. 2-3, in the unexpanded state the cells 220 are all uniform in shape and size.

In at least some embodiments, the expandable frame 200 of a design such as the frame shown in FIGS. 2-4 is supra-annular. As a result of supra-annular design of the expandable frame 200, a valve prosthesis utilizing this frame may have reduced pressure gradients and increased effective orifice area during forward flow and therefore superior hemodynamics.

Figure 5:
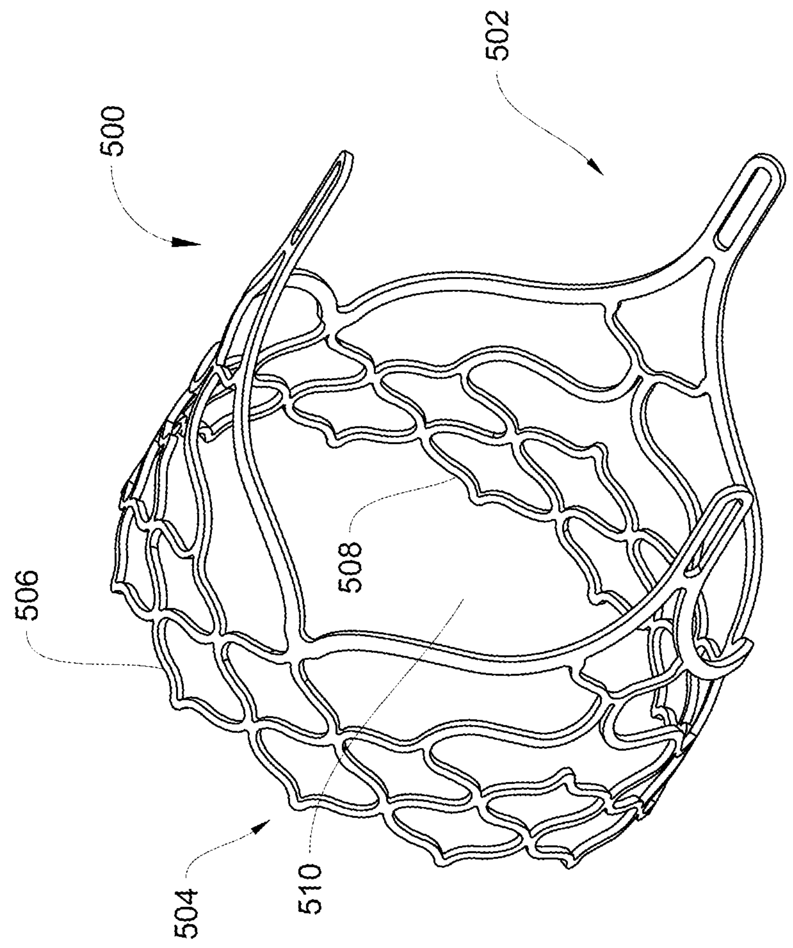
FIG. 5 is a perspective view of the expandable frame in an expanded state, in accordance with at least one embodiment of the present disclosure.
Figure 6:
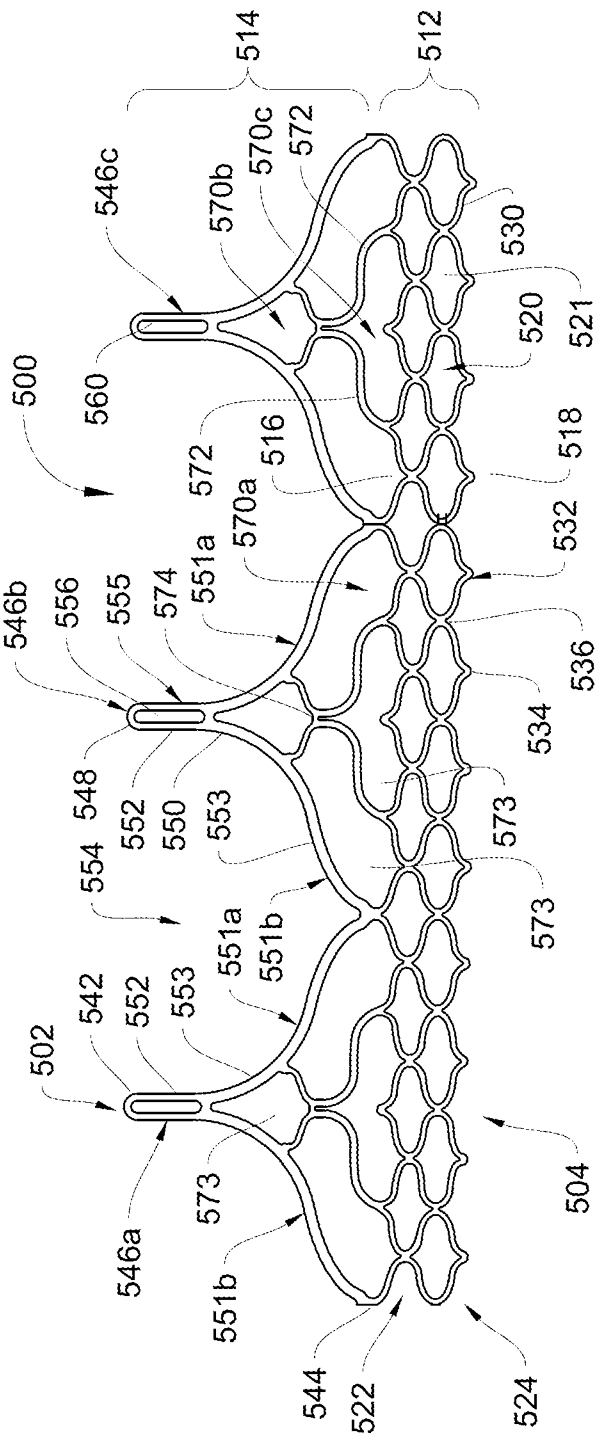
FIG. 6 is a flat, schematic diagram of the expandable frame shown in FIG. 5 in an expanded state.
Figure 7:
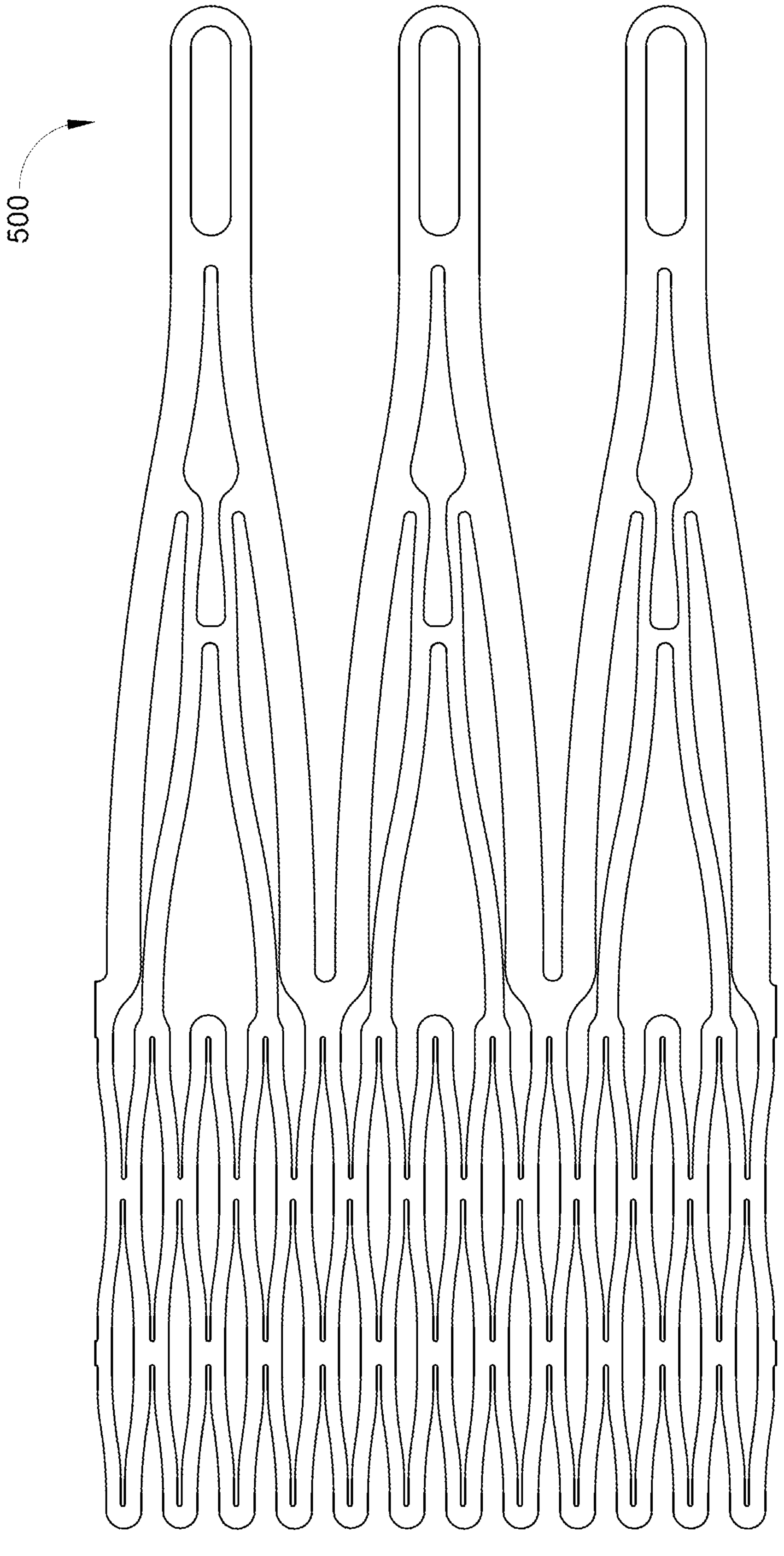
FIG. 7 is a flat, schematic diagram of the expandable frame shown in FIG. 5, in an unexpanded state.

FIGS. 5-7 depict a variation of the expandable frame shown in FIGS. 2-4. FIG. 5 shows a perspective view of the expandable frame 500 in the expanded state. FIG. 6 shows a schematic diagram of the flat, stent pattern of the expandable frame 500 of FIG. 5 in the expanded state, while FIG. 7 shows a schematic diagram of the flat stent pattern of the expandable frame 500 of FIG. 5 in the unexpanded state. In some embodiments, a valve construct (not shown) is mounted to the exterior of the expandable frame 500 shown in FIGS. 5-7, and in other embodiments, the valve construct (not shown) may be mounted to the interior of the frame 500.

Expandable frame 500 may have a proximal end 502 and a distal end 504 opposite the proximal end 502, with an axial length of the expandable frame spanning between the proximal end 502 and the distal end 504. The expandable frame 500 may have an exterior surface 506 and an interior surface 508 with a thickness therebetween. The interior surface 508 defines a lumen 510. Expandable frame 500 may have an expandable region 512 and a cusp region 514 proximal to the expandable region 512. The cusp region 514 allows for the leaflets of the valve construct to open beyond the exterior surface 506, and in some embodiments more particularly allow for the leaflets to open beyond the exterior surface 506 of at least the expandable region 512 of the expandable frame, which may be considered to be the ventricular section of the frame. This effectively may result in a tapered effect, where the area defined by a free edge of the leaflets of the valve construct is larger than the area defined by the exterior surface of the frame, resulting in reduced pressure gradients and increased effective orifice area during forward flow. Prior art valve prostheses do not allow the leaflets to open beyond the exterior surface of the expandable frame because of the frame's cell structure.

The expandable region 512 has a proximal end 516 and a distal end 518. The expandable region 512 comprises a plurality of cells 520 defining openings 521. In the embodiment shown in FIGS. 5-6, the openings 521 have different sizes and shapes. In other embodiments, the openings 521 may all have the same size and shape.

Cells 520 may be arranged into at least a first row of circumferentially adjacent cells, shown generally at 522, at a proximal end 516 of the expandable region 512 and a second row of circumferentially adjacent cells, shown generally at 524, at a distal end 518 of the expandable region 512. As shown in FIGS. 5-7, only these two rows of cells 522, 524 are provided, although in other embodiments a middle row of circumferentially adjacent cells may be provided as described in other embodiments herein.

Each cell 520 comprises a plurality of struts 530. Each strut 530 may be a straight strut or, as shown at least in FIGS. 5-7, may be a curved strut or each strut may be a serpentine strut with at least one turn or undulation. Each strut 530 may have a thickness that may be uniform or may vary over the length of the strut 530. Each strut 530 of the cell 520 may be connected to an adjacent strut at a node 532. Nodes 532 may include end nodes 534 at the proximal end 516 and distal end 518 of the expandable region that connect circumferentially adjacent struts 530 at each end 516, 518. Nodes 532 may also include row nodes 536 that either connect circumferentially adjacent struts 530 in a row 522, 524.

Turning now to the cusp region 514, which is intended to facilitate or assist with movement of the leaflets of a valve construct attached to the expandable frame 500, the cusp region 514 has a proximal end 542 and a distal end 544 adjacent the expandable region 512. The cusp region 514 comprises a plurality of posts 546 for attachment of the valve construct to the expandable frame 500. In some embodiments, the cusp region 514 may have two posts 546. In some embodiments, such as the embodiment shown in FIGS. 5-7, the cusp region 514 may have three posts 546. In still other embodiments, the cusp region 514 may have any number of posts 546.

Each post 546 may have a distal end 548 and a proximal end 550, where the proximal end 550 defines the proximal end 542 of the cusp region 542. In the embodiment shown in FIGS. 5-7, the distal end 548 of the post 546 may be attached to one or more cusp struts 551 of the cusp region 514, and each cusp strut 551 may be attached to the expandable region 512 at one or more end nodes 532. As shown more particularly at least in FIG. 6, each post 546 may be connected to a right cusp strut **551*a* and a left cusp strut 551*b*. In at least the embodiment shown, the combination of the post 546, the right cusp strut 551*a* and the left cusp strut 551*b* creates a wishbone-like structure. In the embodiment shown, the right cusp strut 551*a* of a first post 548*a* and the left cusp strut 551*b* of a second post 548*b* (which is circumferentially adjacent to the first post 548*a*) are connected to the same end node 534 of the expandable region 512. The posts 548 each have a side surface 552 and the right cusp struts each have side surface 553. The side surface 552 of the post 546*a*, the side surface 552 of the post 546*b*, the side surface 553 of the right cusp strut 251*a*, the side surface 553 of the left cusp strut 251*b* that is circumferentially adjacent the right cusp strut 251*b* define leaflet opening 554. The leaflet opening 554 allows the leaflets of the valve construct to traverse the exterior surface of the frame. The leaflet opening 554** may also allow for improved coronary access.

Each post 546 may comprise at least one strut 555, which may include at least one attachment feature 556 disposed within the strut 255. The strut 555 may have a width that is greater than a width of at least one strut 530 of the expandable region 514. In at least the embodiment shown in FIG. 3, the attachment feature 556 may comprise a slot 560. In still other embodiments, the attachment feature 554 may comprise one opening or may comprise a plurality of openings 560 that facilitate a specific suture pattern, said openings being comprised of holes, slots, or slits. In other embodiments, the at least one attachment feature may comprise hooks, loops, pledgets, or other similar attachment features. In some embodiments, the posts 546 and/or the attachment features 554 may further be utilized for recapturing or repositioning of the frame during or after deployment. In some embodiments, the posts 546, the attachment features 554, and/or one or more cusp struts 551 may be utilized for valve-in-valve procedures to either engage with a previously implanted valve prosthesis or to engage with a valve prosthesis being implanted.

The cusp region 514 may further comprise one or more cusp region cells 570, which may be defined by one or more cusp connector struts 572. The cusp connector struts 572 may provide some additional structure to the post 546 to handle stresses incurred by the cusp region as the valve pulsates between systolic and diastolic phases. As shown in FIGS. 5-6, the cusp region cells 570 have openings 573 that are larger than the openings 521 of cells 520. Some of the cusp region cells **570*a* may be defined, in some embodiments, by at least one cusp strut 551, at least one cusp connector strut 572, and one or more struts 530 at the proximal end 516 of the expandable region 512. Other cusp region cells 570*b* may be defined, in some embodiments, by at least two cusp struts 551 and two cusp connector struts 252. Still other cusp region cells 570*c* may be defined, in some embodiments, by at least four struts 5300 of the proximal end 616 of the expandable region 212 and two cusp connector struts 572. Circumferentially adjacent cusp connector struts may further be connected to one another by a node or a small strut as shown at 274**.

In some embodiments, the axial length of the cusp region 514 in the expanded state shown in FIGS. 5-6 is between about 25% and 75% of the axial length of the expandable frame 200. In some embodiments, the axial length of the cusp region 514 in the expanded state shown in FIGS. 5-6 is between about 45% and 75% of the axial length of the expandable frame 500. In at least one embodiment, the axial length of the cusp region 514 in the expanded state shown in FIGS. 5-6 is between about 60% and 75% of the axial length of the expandable frame 500.

In some embodiments, a diameter of the cusp region 514 may be greater than a diameter of the expandable region 512. In some embodiments, the diameter of the cusp region 514 at a proximal end of the cusp region 514 may be similar to the diameter of the expandable region 512 at the distal end of the expandable region 512. In some embodiments, the diameter of the cusp region 514 at a proximal end of the cusp region 514 may be greater than the diameter of the expandable region 512 at the distal end of the expandable region 512. In at least one embodiment, the diameter of the cusp region 514 may be greater at the proximal end of the cusp region than at the distal end of the cusp region, such that the cusp region 514 has a tapered profile in the expanded state.

In some embodiments, a skirt or other paravalvular leak reduction feature may be attached to the exterior surface of the expandable frame 206.

FIG. 7 shows the expandable frame 500 in an unexpanded state. As shown in FIG. 4, the end nodes 532 at the distal end 518 of the frame 500 are all radially aligned. As shown in FIG. 7, the row nodes 536 are also all radially aligned, as are the end nodes 532 at the proximal end 516 of the expandable frame 500. Unlike how the cells 520 of the expandable region 212 appear in their expanded state as shown in FIGS. 5-6, in the unexpanded state the cells 520 are all uniform in shape and size. More particularly, all of the cells in the first circumferential row of cells 522 appear to be the same shape and size in the unexpanded state, whereas as shown in FIGS. 5-6 the cells 520 vary in shape within the first circumferential row of cells 522.

In some embodiments, the valve prosthesis with the expandable frame shown in FIGS. 2-7 has a mean effective orifice area (EOA) between 2.38 $cm^2$ and 3.76 $cm^2$. In some embodiments, the mean EOA may be between 2.64 $cm^2$ and 3.53 $cm^2$. In still other embodiments, the mean EOA may be between 2.84 $cm^2$ and 3.30 $cm^2$. In at least one embodiment, the valve prosthesis 100 has a mean EOA between about 2.5 and 3.5 $cm^2$ and a pressure gradient between about 4-10 mm Hg with a Doppler Velocity Index factor (DVI) between 0.55 and 0.70.

Figure 8:
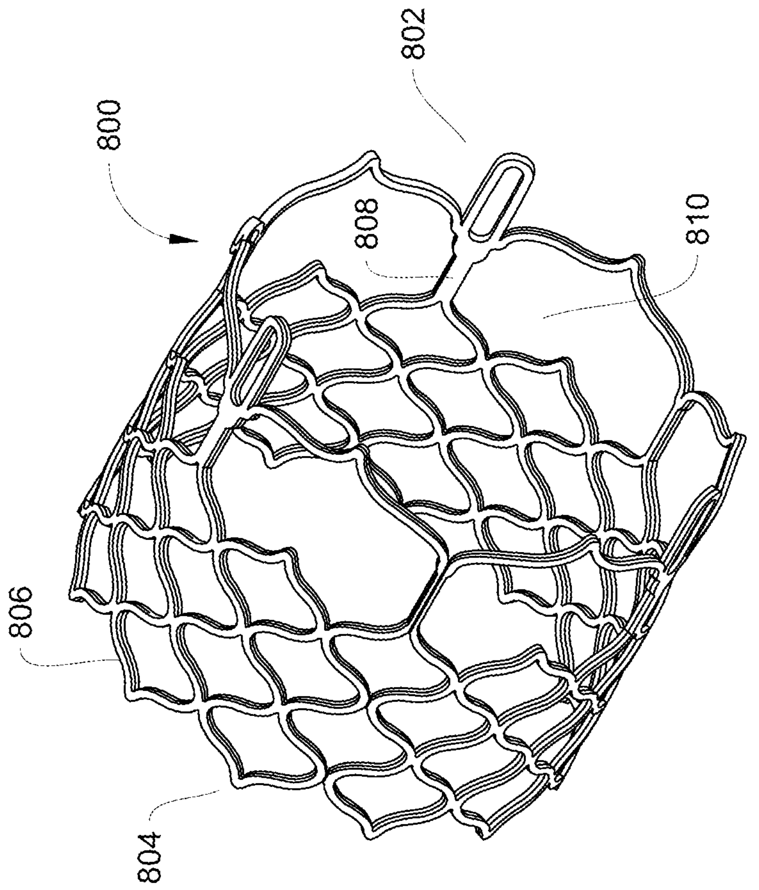
FIG. 8 is a perspective view of the expandable frame in an expanded state, in accordance with at least one embodiment of the present disclosure.
Figure 9:
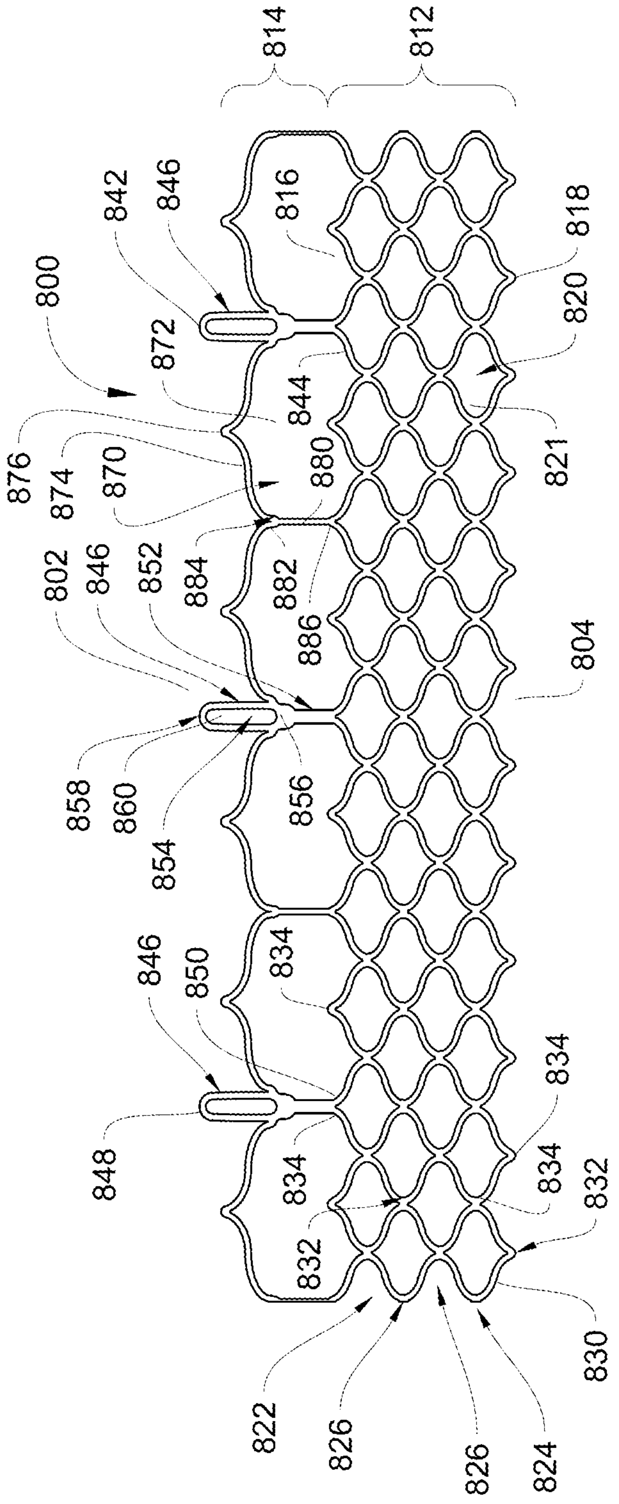
FIG. 9 is a flat, schematic diagram of the expandable frame shown in FIG. 8 in an expanded state.
Figure 10:
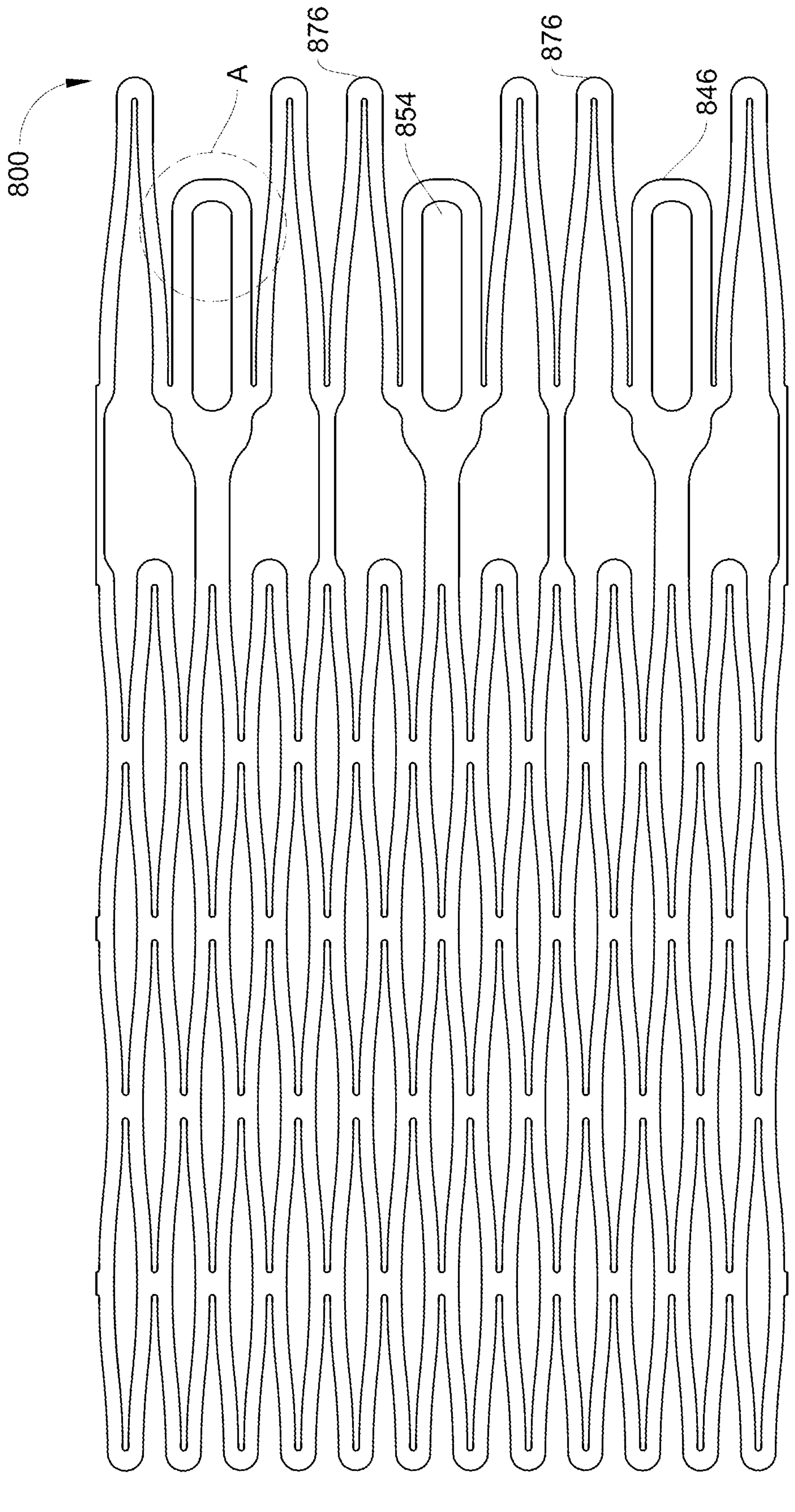
FIG. 10 is a flat, schematic diagram of the expandable frame shown in FIG. 8, in an unexpanded state.

FIGS. 8-10 depict another embodiment of an expandable frame 800 of the present invention. The expandable frame 800, when used with a valve construct as discussed above, can create a shorter, supra-annular valve prosthesis. Coaptation of the valve construct in this expandable frame may be between 45% and 70% of the height of the leaflets. Unlike some of the other embodiments described herein, the expandable frame 800 shown in FIGS. 8-10 is primarily designed for a valve construct to be mounted adjacent to the interior surface of the expandable frame 800. FIG. 8 shows a perspective view of the expandable frame 800 in the expanded state. FIG. 9 shows a schematic diagram of the stent pattern of the expandable frame 800 of FIG. 8 in the expanded state, while FIG. 10 shows a schematic diagram of the stent pattern of the expandable frame 800 of FIG. 8 in the unexpanded state.

Expandable frame 800 may have a proximal end 802 and a distal end 804 opposite the proximal end 802, with an axial length of the expandable frame spanning between the proximal end 802 and the distal end 804. In some embodiments, the axial length of the frame from a proximal end 802 to a distal end 804 is between about 18 mm and 24 mm. The expandable frame 800 may have an exterior surface 806 and an interior surface 808 with a thickness therebetween. The interior surface 808 defines a lumen 810. In at least one embodiment, the diameter of the exterior surface 806 of the expandable frame may be greater than the axial length of the frame from a proximal end 802 to a distal end 804. For example, in an embodiment where the outer diameter of the valve is between about 25.5 mm and 26.5 mm, the axial length of the valve from a proximal end 802 to a distal end 804 is between about 20 mm and 22 mm. Expandable frame 800 may have an expandable region 812 and a cusp region 814 proximal to the expandable region 812.

The expandable region 812 has a proximal end 816 and a distal end 818. The expandable region 812 comprises a plurality of cells 820 defining openings 821. In some embodiments, all of the cells 820 of the expandable region 812 may be substantially the same size and shape. In other embodiments, the cells 820 of the expandable region 812 have different sizes and shapes.

Cells 820 may be arranged into at least a first circumferential row of cells, shown generally at 822, at a proximal end 816 of the expandable region 812 and a second circumferential row of cells, shown generally at 824, at a distal end 818 of the expandable region 812. In some embodiments, a plurality of circumferential middle rows of cells, shown generally at 826, may span between the first circumferential row of cells 822 and the second circumferential row of cells 824. As shown in FIG. 9, the expandable frame 800 has two middle rows of cells 826 between the first circumferential row of cells 822 and the second circumferential row of cells 824.

Each cell 820 comprises a plurality of struts 830. Each strut 830 may be a straight strut or, as shown at least in FIG. 9, may be a curved strut or each strut may be a serpentine strut with at least one turn or undulation. Each strut 830 may have a width that may be uniform or may vary over the length of the strut 830. Each strut of the cell 820 may be connected to an adjacent strut at a node 832. Nodes 832 may include end nodes 834 at the proximal end 816 and distal end 818 of the expandable region that connect circumferentially adjacent struts 830 at each end 816, 818. Nodes 832 may also include row nodes 836 that either connect circumferentially adjacent struts 830 in a row 822, 824, 826 or connect axially adjacent struts 830 of one row 822, 824, 826 to an axially adjacent row.

The cusp region 814 has a proximal end 842 and a distal end 844. The cusp region 814 comprises a plurality of posts 846 for attachment of the valve construct to the expandable frame 800. In some embodiments, the cusp region 814 may have two posts 846. In some embodiments, such as the embodiment shown in FIGS. 8-10, the cusp region 814 may have three posts 846. In still other embodiments, the cusp region may have any number of posts 846. Each post 846 may have a proximal end 848 and a distal end 850 that span from the proximal end 842 to the distal end 844 of the cusp region 814. In some embodiments, the distal end 850 of the post 846 may be attached to an end node 834 at the proximal end 816 of the expandable region 812. In other embodiments, the distal end 848 may be attached a strut 830 of the expandable regions, and more particularly to a strut of at least one cell 820 of the first circumferential row of cells 822. Each post 846 may comprise at least one strut 852 and at least one attachment feature 854 connected to the strut 852. The strut 852 of the post is attached at one end to the expandable region 812. The strut 852 may have a width that is greater than a width of at least one strut 830 of the expandable region 814. The strut 852 may comprise a neck region 856 at a proximal end of the strut 852 that connects strut 852 to the at least one attachment feature 854 of the post 846. The at least one attachment feature 854 may comprise a tab 858 with at least one opening 860 disposed within the tab 858. As shown in FIG. 8, the tab 858 may have a width that is greater than a width of strut 852. In at least the embodiment shown in FIG. 8, the opening 860 may be a slot. In other embodiments, the opening 860 may be a hole. In still other embodiments, the attachment feature 854 may have a plurality of openings 860 that facilitate a specific suture pattern, said openings being comprised of holes, slots, or slits. In other embodiments, the at least one attachment feature may comprise hooks. In some embodiments, the posts 846 may further be utilized for recapturing or repositioning of the frame after deployment.

Each post 846 defines at least a portion of at least one cusp region cells 870. As shown in FIGS. 8-9, the cusp region cells 870 have openings 872 that are larger than the openings 821 of cells 820. The cusp region cells 870 may allow for improved coronary access of the valve prosthesis 800 in some embodiments. The cusp region cells 870 are defined by the struts 830 at the proximal end 816 of the expandable region 812, at least one post 846 and at a pair of cusp struts 874. Each cusp strut 874 may be a straight strut or, as shown at least in FIG. 9, may be a curved strut or each cusp strut may be a serpentine strut with at least one turn or undulation. In some embodiments, the cusp region cells 870 are defined by the strut 852 of the post 846. Each strut 874 forming the pair of cusp struts are connected to one another at a cusp node 876. In some embodiments, a cusp region cell 870 may be further defined by an axial strut 880. Axial strut 880 may be circumferentially adjacent to post 846, as shown in FIG. 9. Axial strut 880 may, at a first end 882, connect one of the struts of the pair of cusp struts at a connecting node 884, and at a second end 886 connect to an end node 834. Axial strut 880 may be a straight strut as shown at least in FIG. 9, or it may be a curved strut or a serpentine strut with at least one turn or undulation. In at least the embodiment shown in FIGS. 8-9, the cusp region cells are defined by eight struts: the strut 852 of the post 846, the pair of cusp struts 874, the axial strut 880, and four adjacent struts 830 of the first circumferential row of cells 822 at a proximal end 816 of the expandable region 812. At least as shown in FIGS. 8-9, the openings 872 of cusp region cells 870, in some embodiments, may form a generally heart-shaped perimeter in the expanded state shown in FIGS. 8-9.

In some embodiments, the axial length of the cusp region 814 in the expanded state shown in FIGS. 8-9 is between about 25% and 75% of the axial length of the expandable frame 800. In some embodiments, the axial length of the cusp region 814 in the expanded state shown in FIGS. 8-9 is between about 30% and 50% of the axial length of the expandable frame 800. In at least one embodiment, the axial length of the cusp region 814 in the expanded state shown in FIGS. 8-9 is between about 40% and 45% of the axial length of the expandable frame 800.

FIG. 10 shows the expandable frame 800 in an unexpanded state. As shown in FIG. 10, the end nodes 832 at the distal end 818 of the frame 800 are all radially aligned. As shown in FIG. 10, the row nodes 836 are also all radially aligned, as are the end nodes 832 at the proximal end of the expandable frame 800. In addition, the row nodes 836 are axially aligned with an adjacent row node of the axially adjacent row of cells. In the unexpanded state, the cusp nodes 876 may be proximal to the proximal end 850 of the post 846, even though in the expanded state the cusp nodes 876 are distal to the proximal end 850 of the post 846 as shown in FIG. 9. Further, in the unexpanded state shown in FIG. 10, the cusp nodes 876 may be proximal to the attachment feature 854. In some embodiments, the cusp nodes 876 may have retrieval features for recapture or repositioning of the expandable frame 800 because the nodes 876 position relative to the attachment feature 854 or the post 846 between the unexpanded and expanded state.

Figure 11:
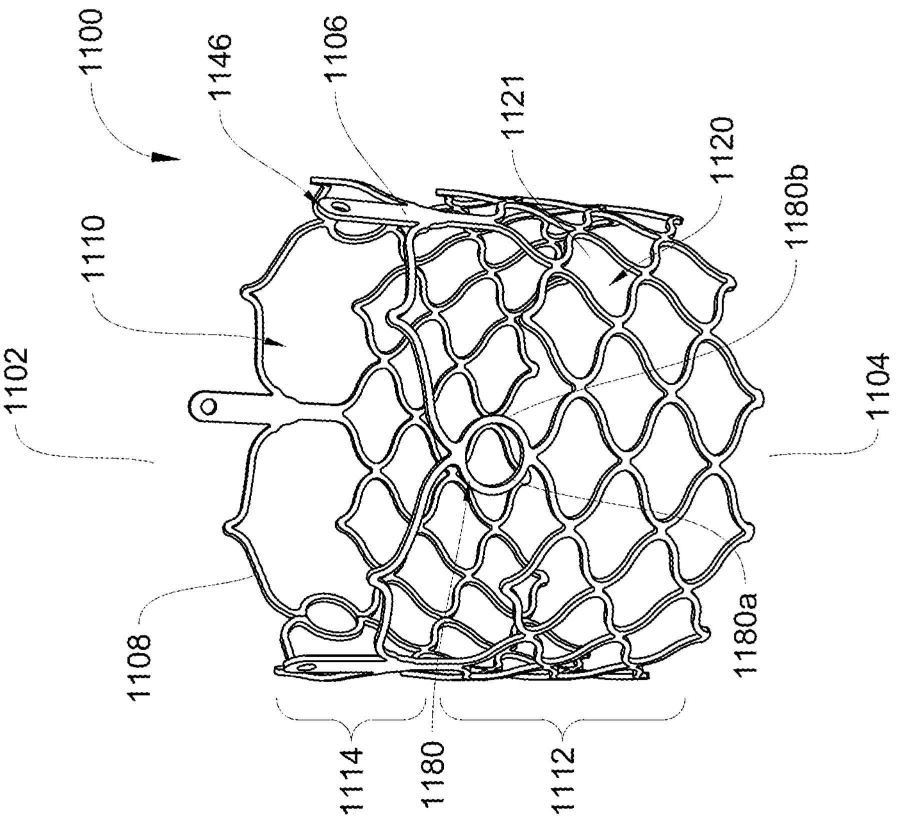
FIG. 11 is a perspective view of the expandable frame in an expanded state, in accordance with at least one embodiment of the present disclosure.
Figure 12:
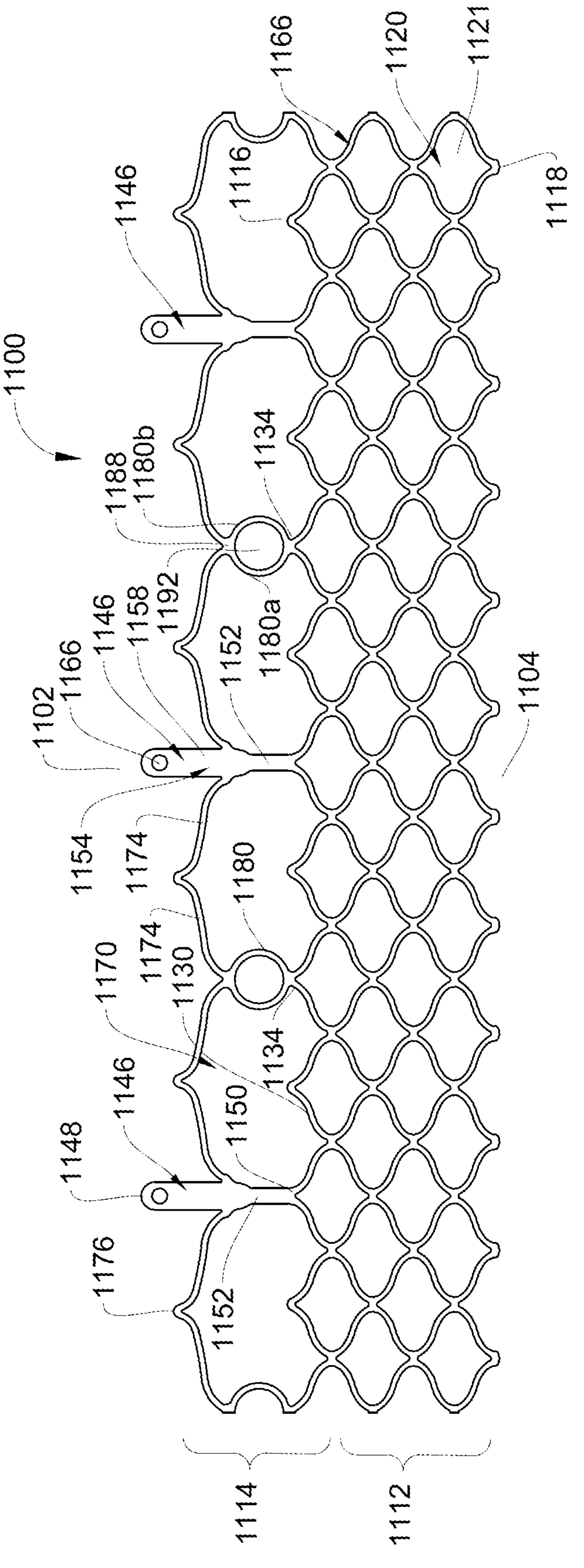
FIG. 12 is a flat, schematic diagram of the expandable frame shown in FIG. 11 in an expanded state.
Figure 13:
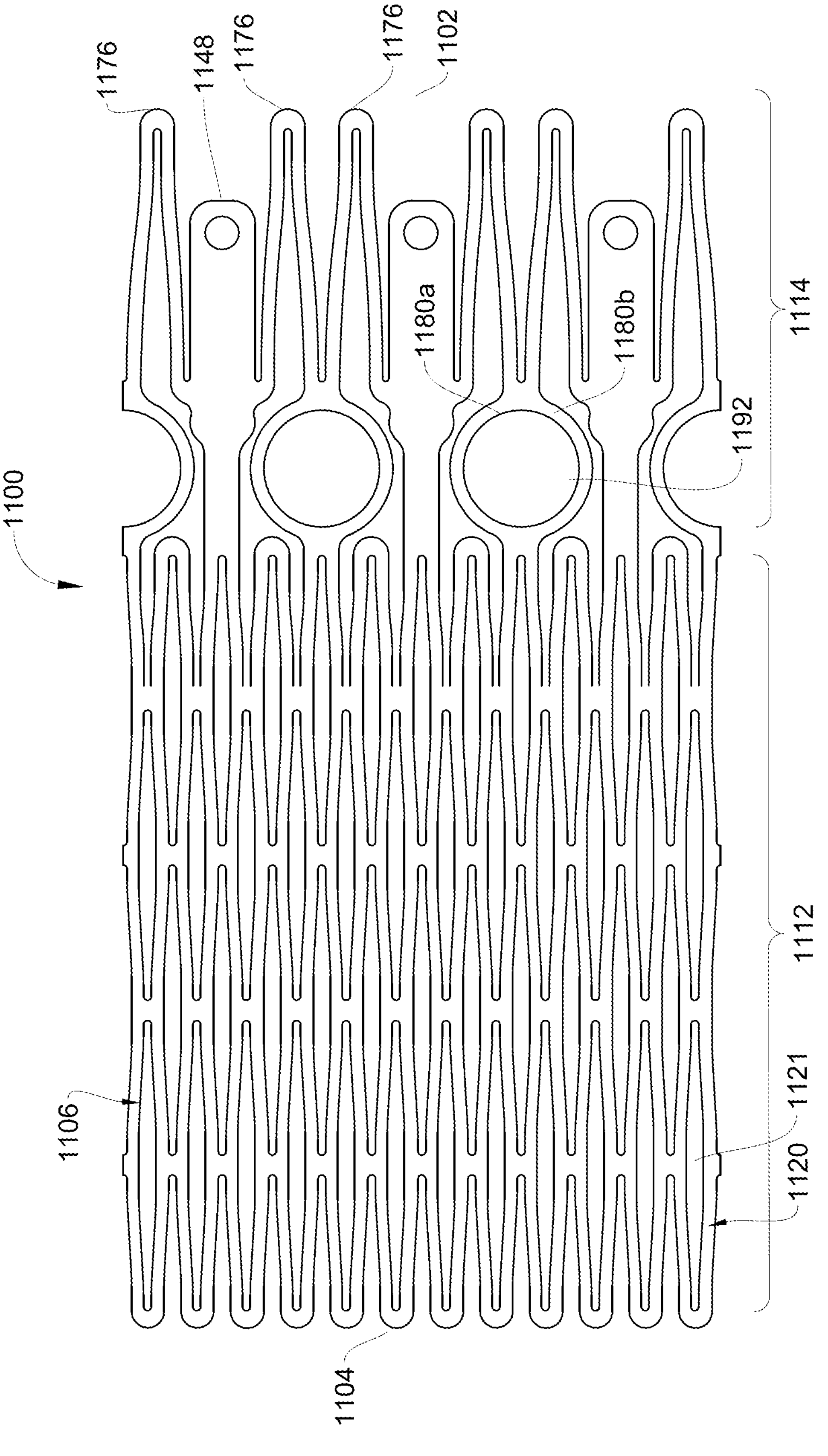
FIG. 13 is a flat, schematic diagram of the expandable frame shown in FIG. 11, in an unexpanded state.
Figure 14A:
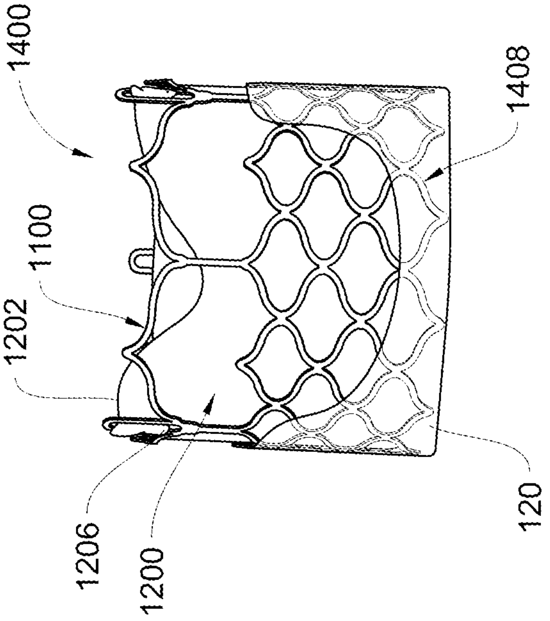
FIG. 14A is a front view of a valve prosthesis with a valve construct mounted to the expandable frame of FIG. 11, in accordance with at least one embodiment of the present disclosure.
Figure 14B:
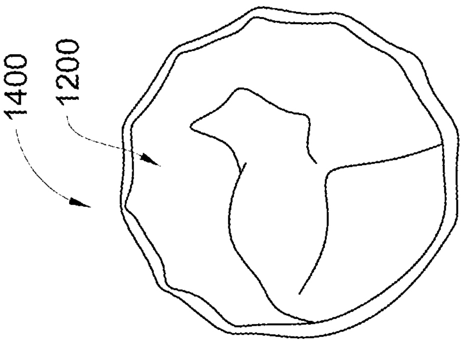
FIG. 14B is a top view of the valve prosthesis shown in FIG. 14A.
Figure 14C:
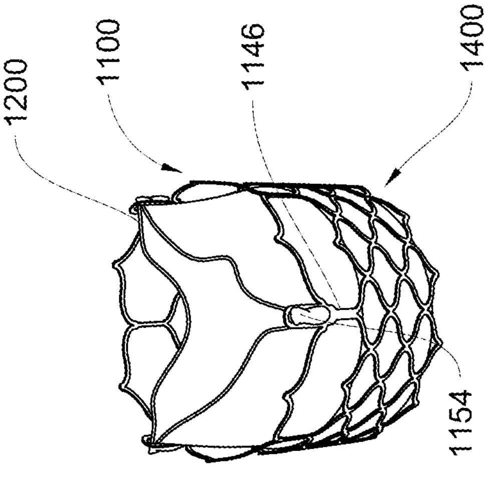
FIG. 14C is a perspective view of the valve prosthesis shown in FIGS. 14A-14B.

FIGS. 11-13 and FIGS. 14A-14C depict another embodiment of an expandable frame 1100 of the present invention. The expandable frame 1100, when used with a valve construct 1200 similar to a valve construct discussed above and shown in FIGS. 14A-14C attached to expandable frame 1100, can create a shorter, supra-annular valve prosthesis 1400. Like the expandable frame shown in FIGS. 8-10, the expandable frame 1100 is primarily designed for a valve construct to be mounted adjacent to the interior surface of the expandable frame 1100 (as particularly shown in FIGS. 14A-C). FIG. 11 shows a perspective view of the expandable frame 1100 in the expanded state. FIG. 12 shows a schematic diagram of the stent pattern of the expandable frame 1100 of FIG. 11 in the expanded state, while FIG. 13 shows a schematic diagram of the stent pattern of the expandable frame 1100 of FIG. 11 in the unexpanded state. FIGS. 14A-14C shows a valve prosthesis 1400 with a valve construct 1200 attached to the expandable frame 1100 shown in FIGS. 11-13.

Expandable frame 1100 may have a proximal end 1102 and a distal end 1104 opposite the proximal end 1102, with an axial length of the expandable frame spanning between the proximal end 1102 and the distal end 1104. The expandable frame 1100 may have an exterior surface 1106 and an interior surface 1108 with a thickness therebetween. The interior surface 1108 defines a lumen 1110. Expandable frame 1100 may have an expandable region 1112 and a cusp region 1114 proximal to the expandable region 1112. The expandable region 1112 has a proximal end 1116 and a distal end 1118. The expandable region 1112 comprises a plurality of cells 1120 defining openings 1121. In some embodiments, all of the cells 1120 of the expandable region 1112 may be substantially the same size and shape. In other embodiments, the cells 1120 of the expandable region 1112 have different sizes and shapes. The cells 1120 may be arranged as discussed above for the cells 820 of the embodiment shown in FIGS. 8-10.

The cusp region 1114 may have a proximal end 1142 and a distal end 1144. The cusp region 1114 comprises a plurality of posts 1146 for attachment of the valve construct to the expandable frame 1100. In some embodiments, the cusp region 1114 may have two posts 1146. In some embodiments, such as the embodiment shown in FIGS. 11-14, the cusp region 1114 may have three posts 1146. In still other embodiments, the cusp region may have any number of posts 1146. Each post 1146 may have a proximal end 1148 and a distal end 1150 that span from the proximal end 1142 to the distal end 1144 of the cusp region 1114. In some embodiments, the distal end 1150 of the post 1146 may be attached to the expandable region 1112 at the proximal end 1116 as discussed above for the posts 846 of the embodiment shown in FIGS. 8-10.

Each post 1146 may comprise at least one strut 1152 and at least one attachment feature 1154 connected to the strut 1152. The strut 1152 of the post is attached at one end to the expandable region 1112. The strut 1152 may have a width that is greater than a width of a strut of the expandable region 1112. The at least one attachment feature 1154 may comprise a tab 1158 with at least one opening 1160 disposed within the tab 1158. In at least one embodiment, the opening 1160 may be a slot and in other embodiments the opening 1160 may be a hole. In still other embodiments, the attachment feature 1154 may comprise a plurality of openings 1160 that facilitate a specific suture pattern, said openings being comprised of holes, slots, or slits. In other embodiments, the at least one attachment feature may comprise hooks. In some embodiments, the struts 1152 may have retrieval features for recapture or repositioning of the expandable frame 1100.

Each post 1146 defines at least a portion of at least one cusp region cells 1170. The at least one cusp region cells 1170 may be defined similarly to the cusp region cells 870 of the embodiment shown in FIGS. 8-10. In at least the embodiment shown in FIGS. 11-13, the cusp region cells are defined by eight struts: the strut 1152 of the post 1146, a pair of cusp struts 1174, a C-shaped strut 1180 connected to one of the cusp struts 1174 at one end and an end node 1134 of the expandable region 1112, and four adjacent struts 1130 of the first circumferential row of cells 1122 at a proximal end 1116 of the expandable region 1112. Adjacent C-shaped struts 1180*a*, 1180*b* may be connected to the same end node 1134 of the expandable region. The adjacent C-shaped struts 1180*a*, 1180*b* may each respectively be attached to a strut 1174*a*, 1174*b* of adjacent pairs of struts. The connection of the adjacent C-shaped struts 1180*a*, 1180*b* and struts 1174*a*, 1174*b* form a node 1188. The C-shaped struts 1180*a*, 1180*b* of adjacent cusp region cells 1170 form an opening 1192. The opening 1192 may be sized and shaped to allow for coronary access for secondary procedures (such as atherectomy or angioplasty procedures) without obstructing movement of the cusps or leaflets of the valve construct. In some embodiments, the opening 1192 may be between 10 French (10 Fr) and 14 French (14 Fr) in size, and in at least one embodiment, the opening 1192 may be 12 French (12 Fr) in size to allow for the latter insertion of a catheter.

FIG. 13 shows the expandable frame 1100 in an unexpanded state. In the unexpanded state, the cusp nodes 1176 may be proximal to the proximal end 1148 of the post 1146, even though in the expanded state the cusp nodes 1176 are distal to the proximal end 1148 of the post 1146 as shown in FIG. 12. The cusp nodes 1176 may be radially aligned. As shown in FIG. 13, the openings 1192 may be radially aligned in the unexpanded state. In some embodiments, adjacent nodes 1188 may be radially aligned in the unexpanded state.

FIGS. 14A-14C depict the attachment of a valve construct 1200 to the expandable frame 1100 according to at least one embodiment of a valve prosthesis 1400. The valve construct 1200 may be attached to the frame as described in the disclosure of commonly owned U.S. application Ser. No. 16/129,235 and entitled "Replacement Heart Valve with Reduced Suturing," which is incorporated by reference herein in its entirety. Further, the valve construct 1200 may be attached to the expandable frame 1100 by overlapping some of the tissue onto the posts 1146. In one embodiment, a slit 1206 may be created in the valve construct 1200 near each commissural region 1202 of the valve construct and near the proximal end 1204 of the valve construct. Each post 1146 may be inserted through one slit 1206 of the valve construct 1200 so that the commissural region 1202 at least partially overlaps the proximal end of the post 1146. Using sutures, the valve construct can then be attached at each post 1146 using attachment feature 1154. At least one running belly suture using a single suture can be used circumferentially around the frame to further connect the valve construct to the frame. In one embodiment, the running belly suture follows the pattern of the cusps of the valve construct. In some embodiments of the valve prosthesis 1400, a paravalvular leak skirt 1408 may be provided on the outer surface of the valve. The skirt may be attached with another suture circumferentially around the valve. In at least one embodiment, the valve prosthesis 1400 has fewer than six sutures. In some embodiments, the valve prosthesis has between three and six sutures. In other embodiments, the valve prosthesis has between three and five sutures.

Figure 15:
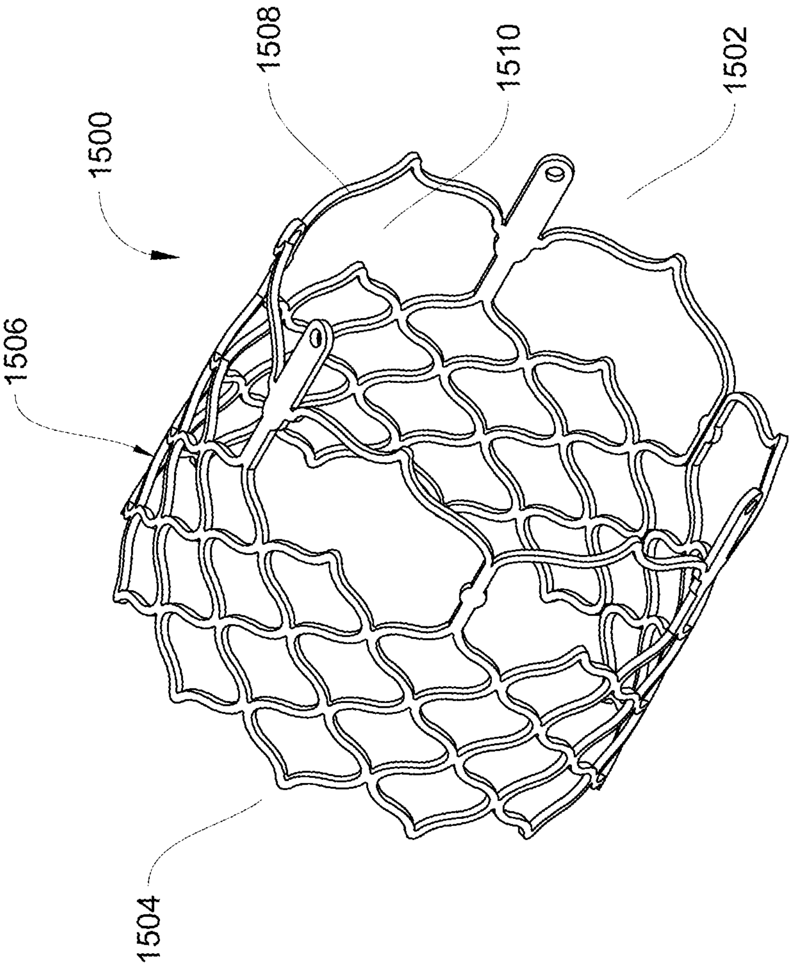
FIG. 15 is a perspective view of the expandable frame in an expanded state, in accordance with at least one embodiment of the present disclosure.
Figure 16:
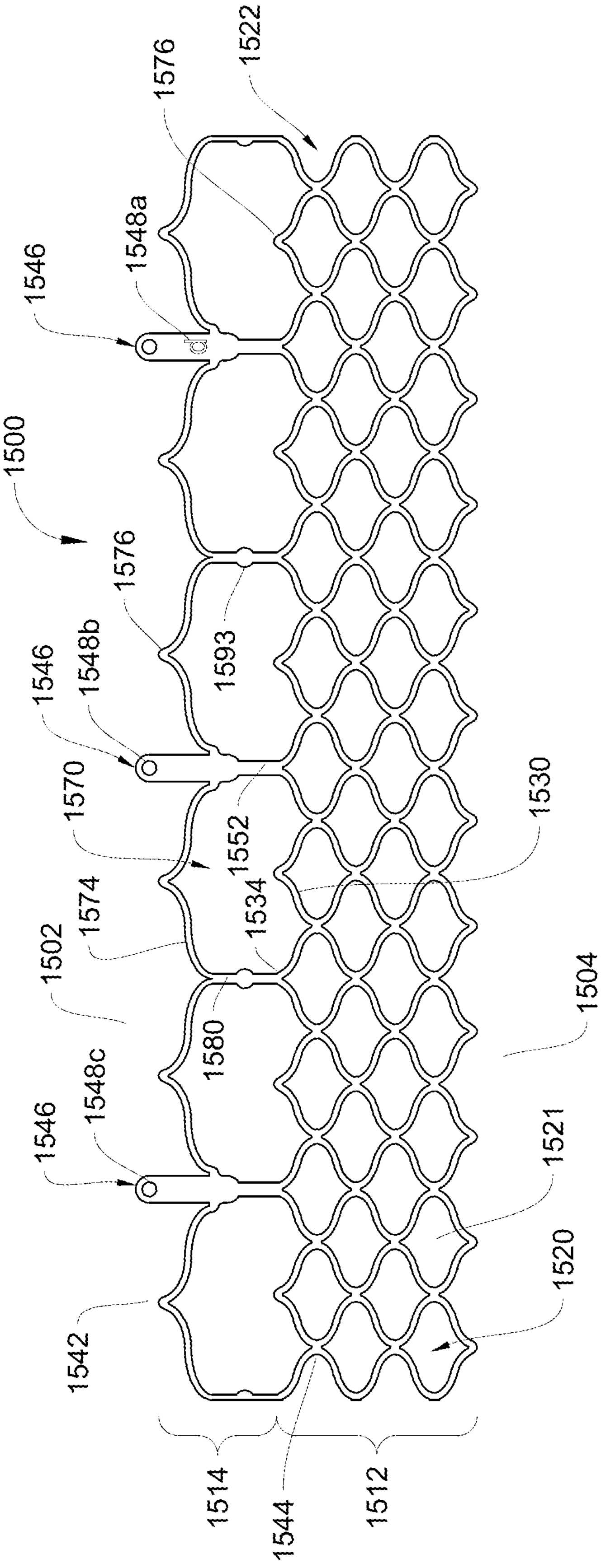
FIG. 16 is a flat, schematic diagram of the expandable frame shown in FIG. 15 in an expanded state.
Figure 17:
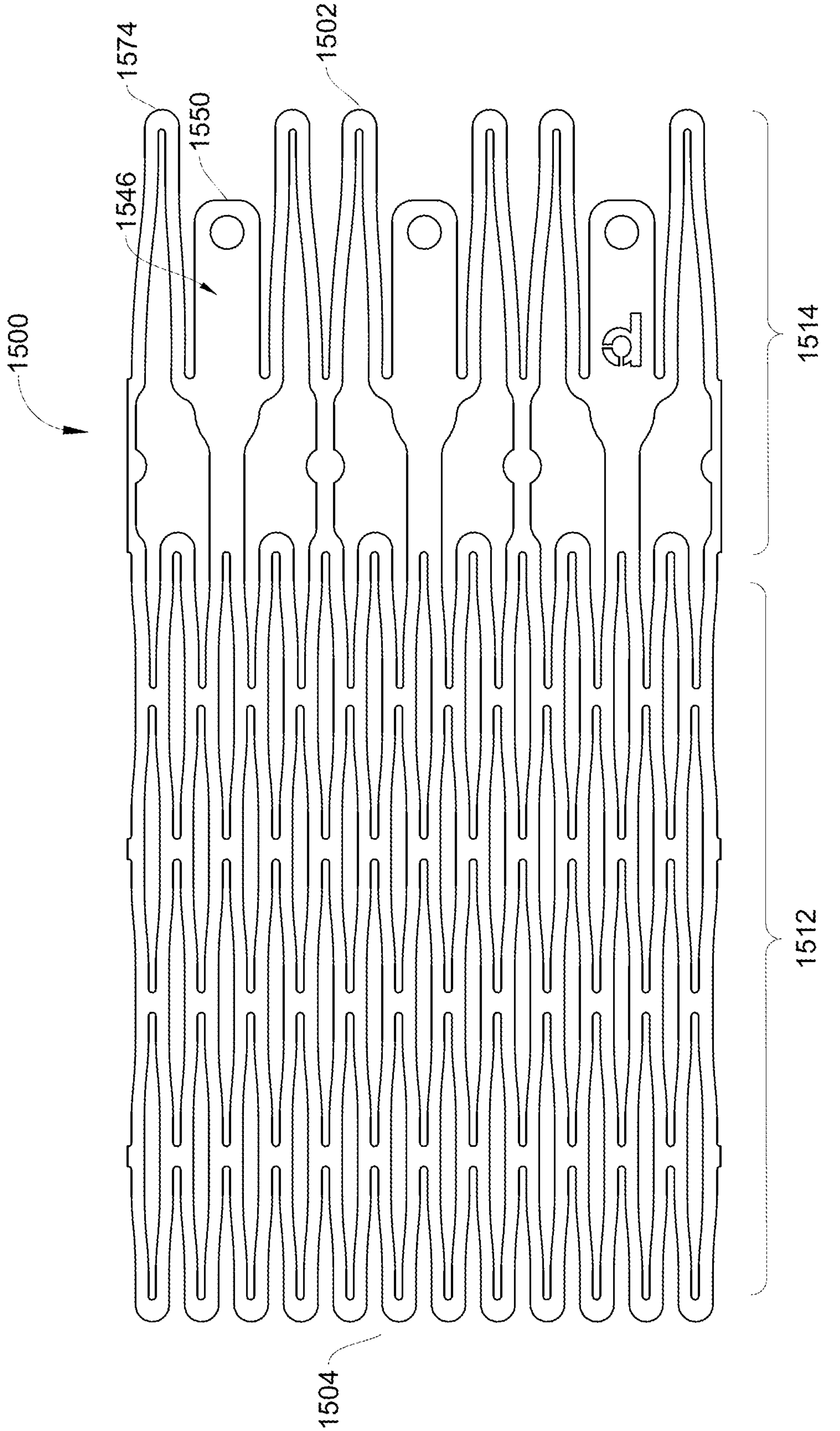
FIG. 17 is a flat, schematic diagram of the expandable frame shown in FIG. 16 in an unexpanded state.

FIGS. 15-17 depict another embodiment of an expandable frame 1500 of the present invention. The expandable frame 1500, when used with a valve construct 1200 as discussed above and shown in FIGS. 14A-14C attached to expandable frame 1150, can create a shorter, supra-annular valve prosthesis. Like the expandable frame shown in FIGS. 8-13, the expandable frame 1500 is primarily designed for a valve construct to be mounted adjacent to the interior surface of the expandable frame 1500.

Expandable frame 1500 may have a proximal end 1502 and a distal end 1504 opposite the proximal end 1502, with an axial length of the expandable frame spanning between the proximal end 1502 and the distal end 1504. The expandable frame 1500 may have an exterior surface 1506 and an interior surface 1508 with a thickness therebetween. The interior surface 1508 defines a lumen 1510. Expandable frame 1500 may have an expandable region 1512 and a cusp region 1514 proximal to the expandable region 1512. The expandable region 1512 has a proximal end 1516 and a distal end 1518. The expandable region 1512 comprises a plurality of cells 1520 defining openings 1521. In some embodiments, all of the cells 1520 of the expandable region 1512 may be substantially the same size and shape. In other embodiments, the cells 1520 of the expandable region 1512 have different sizes and shapes. The cells 1520 may be arranged as discussed above for the cells 820 of the embodiment shown in FIGS. 8-10 and 1120 of the embodiment shown in FIGS. 11-13.

The cusp region 1514 may have a proximal end 1542 and a distal end 1544. The cusp region 1514 comprises a plurality of posts 1546 for attachment of the valve construct to the expandable frame 1500. In some embodiments, the cusp region 1514 may have two posts 1546. In some embodiments, such as the embodiment shown in FIGS. 15-17 the cusp region 1514 may have three posts 1546. In still other embodiments, the cusp region may have any number of posts 1546. Each post 1546 may have a proximal end 1548 and a distal end 1550 that span from the proximal end 1542 to the distal end 1544 of the cusp region 1154. In some embodiments, the distal end 1550 of the post 1546 may be attached to the expandable region 1512 at the proximal end 1516 as discussed above for the posts 846 of the embodiment shown in FIGS. 8-10 and 1146 of the embodiment shown in FIGS. 11-13.

Each post 1546 may comprise at least one strut 1152 and at least one attachment feature 1154 connected to the strut 1152 as discussed above for the posts 1146 of the embodiment shown in FIGS. 11-13. As shown in FIGS. 15-17, the at least one attachment feature may differ from one post 1546 to an adjacent post. As shown in FIGS. 15-17, at least one of the posts **1546*a* may have an attachment feature 1548*a* comprising a plurality of slits 1560 in a pattern. As shown in FIGS. 15-17, the plurality of slits 1560 form a lowercase "d" on one of the posts 1146, but the pattern may also form a capital "D" or any other suitable or desirable configuration. The other posts 1546*b* and 1546*c* may have the same attachment feature 1548*b*, 1548*c* such as a hole or slot that differs from the attachment feature 1548. Having one post 1546*a* with a different attachment feature 1548*a* than any of the attachment features 1548*b*, 1548*c* of any of the other posts (or while the other posts have relatively consistent attachment features) may assist a practitioner with identifying one of the commissural posts to aid with alignment and orientation of the valve during delivery. In at least one embodiment, a first post 1546 may have a pattern of slits, a second post 1546 may have at least one hole, and a third post 1546** may have at least one slot so that each post has a different attachment feature than an adjacent post. This configuration may further assist a practitioner with alignment and orientation of the valve during delivery.

Each post 1546 defines at least a portion of at least one cusp region cells 1570. The at least one cusp region cells 1570 may be defined similarly to the cusp region cells 870 of the embodiment shown in FIGS. 8-10 and the cusp region cells 1170 of the embodiment shown in FIGS. 11-13. In at least the embodiment shown in FIG. 16, the cusp region cells 1570 are defined by eight struts: the strut 1552 of the post 1546, a pair of cusp struts 1574, an axial strut 1580 connected to one of the cusp struts 1574 at one end and an end node 1534 of the expandable region 1512, and four adjacent struts 1530 of the first circumferential row of cells 1522 at a proximal end 1516 of the expandable region 1512. In this embodiment, the axial strut 1580 comprises at least one bump 1593. As shown, the axial strut 1580 has two bumps 1593.

FIG. 17 shows the expandable frame 1500 in an unexpanded state. In the unexpanded state, the cusp nodes 1576 may be proximal to the proximal end 1550 of the post 1546, even though in the expanded state the cusp nodes 1576 are distal to the proximal end 1550 of the post 1546 as shown in FIG. 16. The cusp nodes 1576 may be radially aligned.

Figure 18:
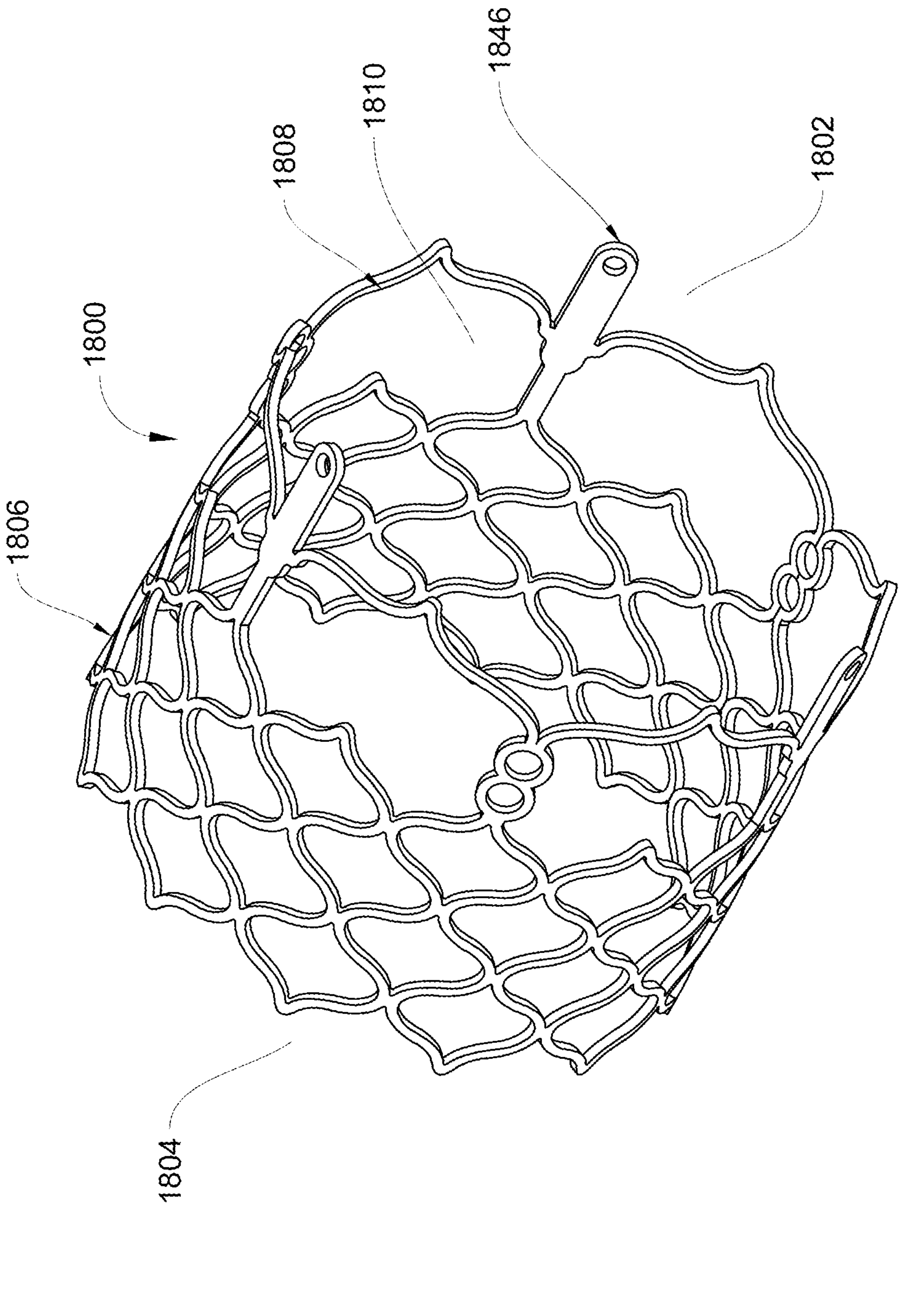
FIG. 18 is a perspective view of the expandable frame in an expanded state, in accordance with at least one embodiment of the present disclosure.
Figure 19:
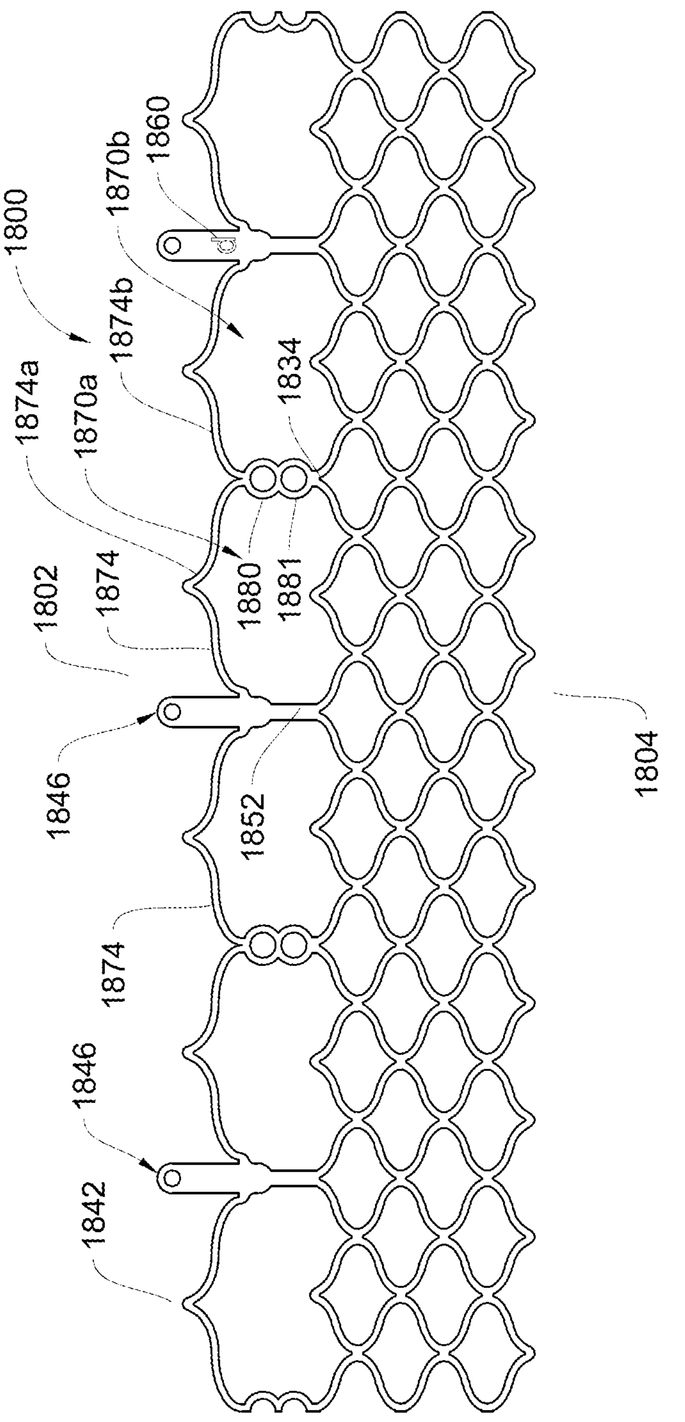
FIG. 19 is a flat, schematic diagram of the expandable frame shown in FIG. 15 in an expanded state.
Figure 20:
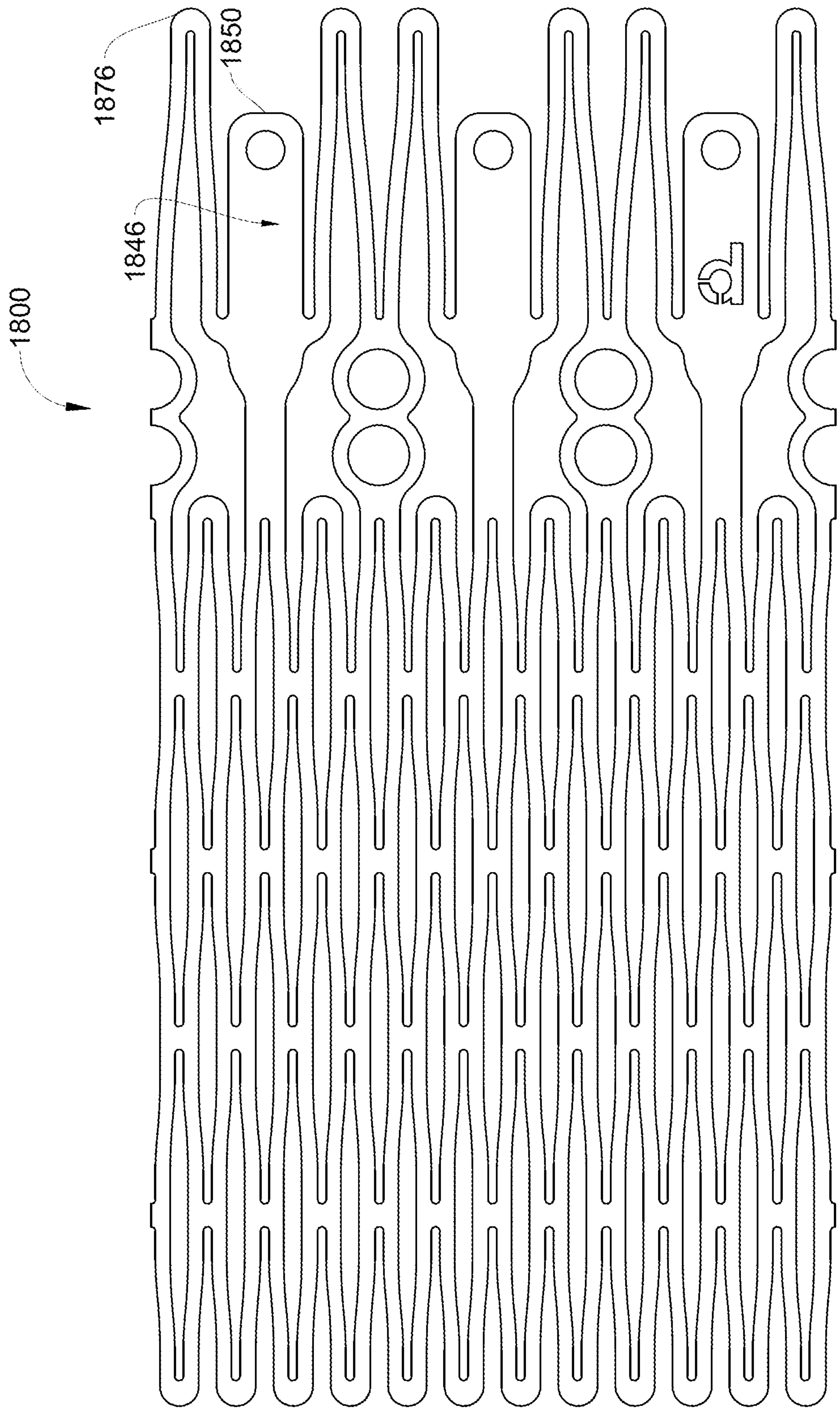
FIG. 20 is a flat, schematic diagram of the expandable frame shown in FIG. 16 in an unexpanded state.

FIGS. 18-20 depict another embodiment of an expandable frame 1800 of the present invention. The expandable frame 1800, when attached to a valve construct as discussed above, can create a shorter, supra-annular valve prosthesis. Like the expandable frame shown in FIGS. 8-17, the expandable frame 1800 is primarily designed for a valve construct to be mounted adjacent to the interior surface of the expandable frame 1800. However, a valve construct could be mounted to the exterior surface of this embodiment or any of the embodiments discussed herein.

Expandable frame 1800 may have a proximal end 1802 and a distal end 1804 opposite the proximal end 1802, with an axial length of the expandable frame spanning between the proximal end 1802 and the distal end 1804. The expandable frame 1800 may have an exterior surface 1806 and an interior surface 1808 with a thickness therebetween. The interior surface 1808 defines a lumen 1810. Expandable frame 1800 may have an expandable region 1812 and a cusp region 1814 proximal to the expandable region 1812. The expandable region 1812 has a proximal end 1816 and a distal end 1818. The expandable region 1812 comprises a plurality of cells 1820 defining openings 1821. In some embodiments, all of the cells 1820 of the expandable region 1812 may be substantially the same size and shape. In other embodiments, the cells 1820 of the expandable region 1812 have different sizes and shapes. The cells 1820 may be arranged as discussed above for the cells 820 of the embodiment shown in FIGS. 8-10 and 1120 of the embodiment shown in FIGS. 11-13.

The cusp region 1814 may have a proximal end 1842 and a distal end 1844. The cusp region 1814 comprises a plurality of posts 1846 for attachment of the valve construct to the expandable frame 1800. In some embodiments, the cusp region 1814 may have two posts 1846. In some embodiments, such as the embodiment shown in FIGS. 18-20, the cusp region 1814 may have three posts 1846. In still other embodiments, the cusp region may have any number of posts 1846. Each post 1846 may have a proximal end 1848 and a distal end 1850 that span from the proximal end 1842 to the distal end 1844 of the cusp region 1854. In some embodiments, the distal end 1850 of the post 1846 may be attached to the expandable region 1812 at the proximal end 1816 as discussed above for the posts 846 of the embodiment shown in FIGS. 8-10 and 1146 of the embodiment shown in FIGS. 11-13.

Each post 1846 may comprise at least one strut 1852 and at least one attachment feature 1854 connected to the strut 1852 as discussed above for the posts 1846 of the embodiment shown in FIGS. 18-20. The at least one attachment feature may differ from one post 1846 to an adjacent post. As discussed above with respect to the embodiment shown FIGS. 15-17, at least one of the posts **1846*a* may have an attachment feature 1848*a* comprising a plurality of slits 1860 in a pattern. In some embodiments, the plurality of slits 1860 form a lowercase "d" on one of the posts 1846, but the pattern may also form a capital "D" or any other suitable or desirable configuration. The other posts 1846*b* and 1846*c* may have the same attachment feature 1848*b*, 1548*c* such as a hole or slot that differs from the attachment feature 1848. In at least one embodiment, a first post 1846 may have a pattern of slits, a second post 1846 may have at least one hole, and a third post 1846** may have at least one slot so that each post has a different attachment feature than an adjacent post. This configuration may assist a practitioner with alignment and orientation of the valve during delivery.

Each post 1846 defines at least a portion of at least one cusp region cells 1870. The at least one cusp region cells 1870 may be defined similarly to the cusp region cells 870 of the embodiment shown in FIGS. 8-10. In at least the embodiment shown in FIGS. 15-17, the cusp region cells 1870 are defined by nine struts: the strut 1852 of the post 1846, a pair of cusp struts 1874, a first serpentine strut 1880, a second serpentine strut 1881, and four adjacent struts 1830 of the first circumferential row of cells 1822 at a proximal end 1816 of the expandable region 1812. In one embodiment, the first serpentine strut 1880 may be connected to one of the cusp struts 1874*a* of the cusp region cell 1870*a* at a first end and an end node 1834 of the expandable region 1812 at a second end. The second serpentine strut 1881 may be connected at a first end to one of the cusp struts 1874*b* of the cusp region cell 1870*b* adjacent to the cusp region cell 1870*a* and the end node 1834 at a second end. The second serpentine strut 1881 may overlap the first serpentine strut 1880 in one embodiment. The overlapping serpentine struts 1880, 1881 may form an "8"-figure shape with two openings. The overlapping serpentine struts 1880, 1881 allow for improved stiffness in the cusp region 1814 and resist twisting in the area.

FIG. 20 shows the expandable frame 1800 in an unexpanded state. Like the other embodiments discussed herein with respect to FIGS. 8-13 and 15-17, in the unexpanded state, the cusp nodes 1876 may be proximal to the proximal end 1850 of the post 1846, even though in the expanded state the cusp nodes 1876 are distal to the proximal end 1850 of the post 1846 as shown in FIG. 19. The cusp nodes 1876 may be radially aligned.

In some embodiments, the valve prosthesis with the expandable frame shown in FIGS. 18-20 has a mean effective orifice area (EOA) between 1.33 $cm^2$ and 3.43 $cm^2$. In some embodiments, the mean EOA may be between 1.68 $cm^2$ and 3.08 $cm^2$. In still other embodiments, the mean EOA may be between 2.03 $cm^2$ and 2.73 $cm^2$.

Figure 21:
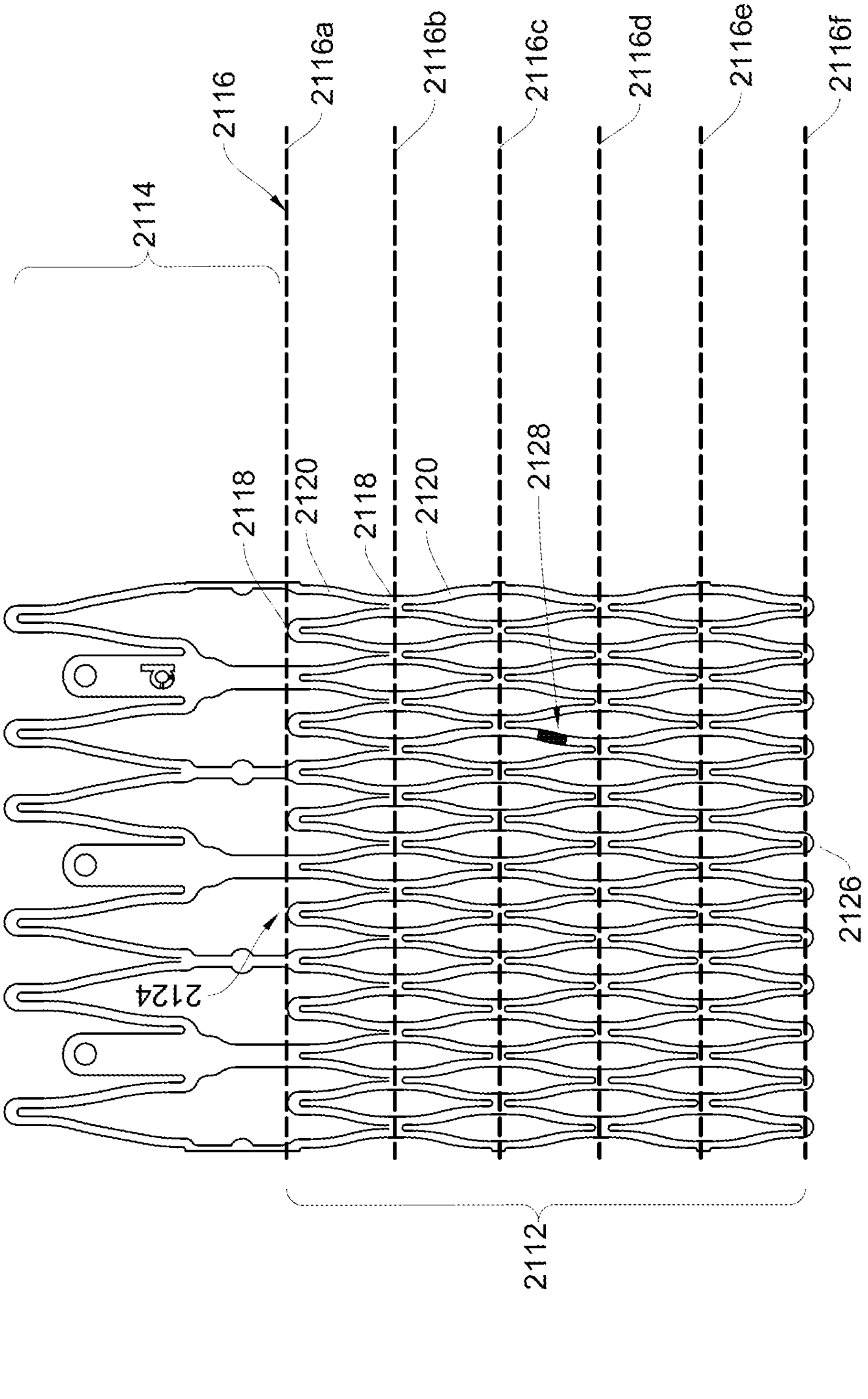
FIG. 21 is a flat, schematic diagram of the expandable frame in the unexpanded state with at least one radiopaque marker, in accordance with at least one embodiment of the present disclosure.

The expandable frames discussed herein may further comprise one or more radiopaque markers for positioning of the expandable frame, and therefore the valve construct, in a desirable position relative to the patient's native anatomy during the delivery procedure. In some embodiments of the expandable frame, including but not limited to those depicted at least in FIGS. 8-20, the expandable frame may have a radiopaque marker attached to at least one strut. In some embodiments of the expandable frame, including but not limited to those depicted at least in FIGS. 8-20, the expandable frame may have a radiopaque marker attached to at least one node. In some embodiments, the radiopaque marker may be positioned on at least one strut or at least one node or combinations of at least one strut or node. In some embodiments, the radiopaque marker may be attached to at least one strut or at least one node or combinations of at least one strut or node. In some embodiments, the radiopaque marker may be a coating on that portion of the expandable frame. The position of the radiopaque marker may be determined by the foreshortening of the strut from its loaded state in the delivery catheter (which may or may not be equivalent to its unexpanded state) to its expanded state. In some embodiments, the position of the radiopaque marker may be determined by the foreshortening of the strut from the unexpanded state to its expanded state. In some embodiments, the radiopaque marker may be positioned in the distal row of the expandable region. In still further embodiments, a radiopaque marker may be placed on at least one of the commissural posts or on a strut or node of the cusp region. In at least one embodiment, as shown in FIG. 21, the expandable frame 2100 may have an expandable region 2112 of cells and a cusp region 2114 of cells proximal to the expandable region 2112. The cusp region 2114 may be define an outflow end of the expandable frame and the expandable region 2112 may define an inflow end of the expandable frame. In at least In the expandable region 2112, the expandable frame 2100 may have a plurality of rows 2116 of nodes 2118 that connect struts 2120 of adjacent cells of the expandable region 2112. As shown in FIG. 21, the expandable region 2112 has five rows 2116*a*, 2116*b*, 2116*c*, 2116*d*, and 2116*e* of nodes 2118. Row 2116*a* may define a proximal end 2124 of the expandable region 2112, and row 2116*e* may define a distal end 2126 of the expandable region 2112. In some embodiments, a radiopaque marker may be positioned at one of the end rows 2116*a*, 2116*e*. More particularly, a radiopaque marker may be positioned at or near a node of row 2116*e* to assist a practitioner in visualizing the position of the distal end of the expandable frame during delivery. In other embodiments, a radiopaque marker may be positioned at or near a node of row 2116*a* near the outflow end of the valve prosthesis to assist a practitioner in visualizing the relative position of the valve cusps of the valve construct. In other embodiments, a radiopaque marker may be positioned in a middle row 2116*b*, 2116*c*, 2116*d* of nodes of the expandable region 2112. More particularly, as shown in FIG. 21, a radiopaque marker 2128 may be positioned on a strut 2120 between row 2116*c* and 2116*d*. The position of the radiopaque marker 2128, in some embodiments, may translate to the desired position of the expandable frame relative to the patient's native annulus so that it may be properly positioned supra-annularly relative to the patient's native annulus.

Figure 22:
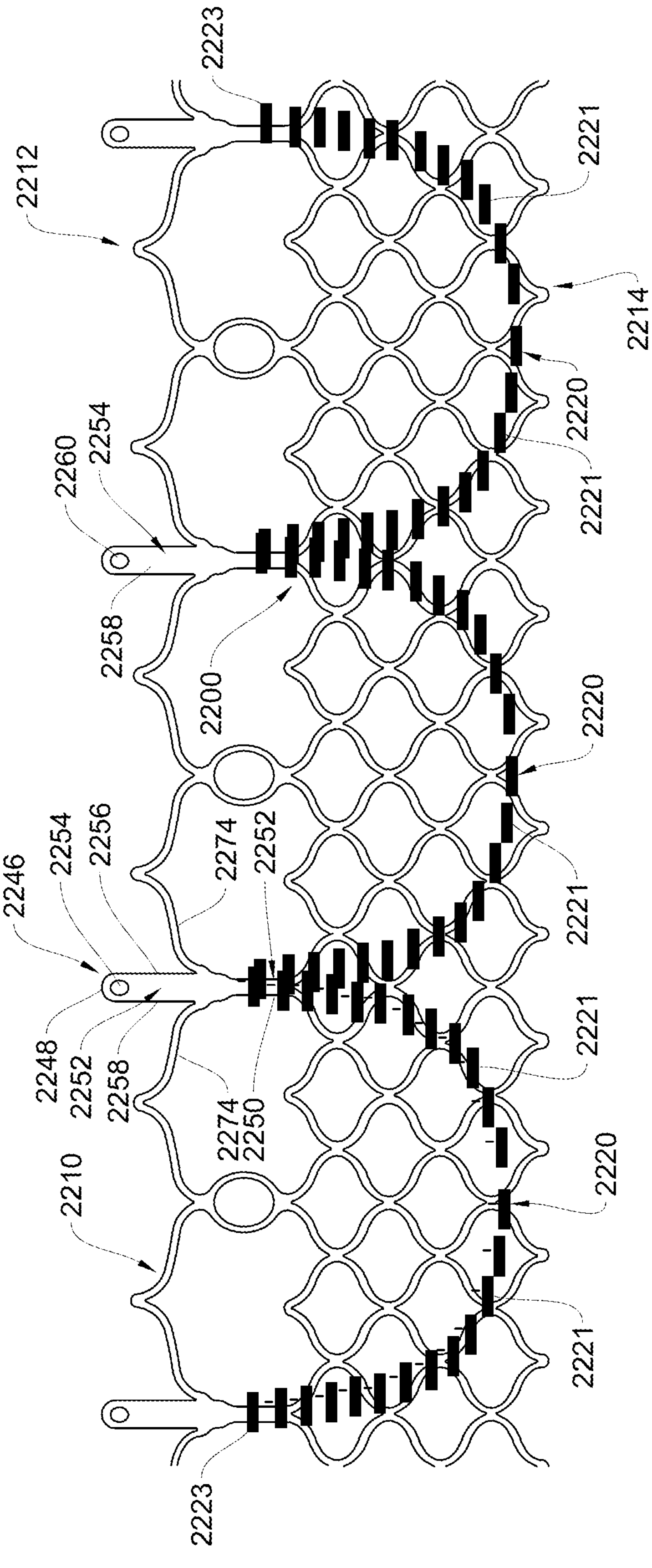
FIG. 22 is a flat, schematic diagram of the expandable frame and the suture pattern used to attach the tissue to at least a portion of the expandable frame, in accordance with at least one embodiment of the present disclosure.
Figure 23:
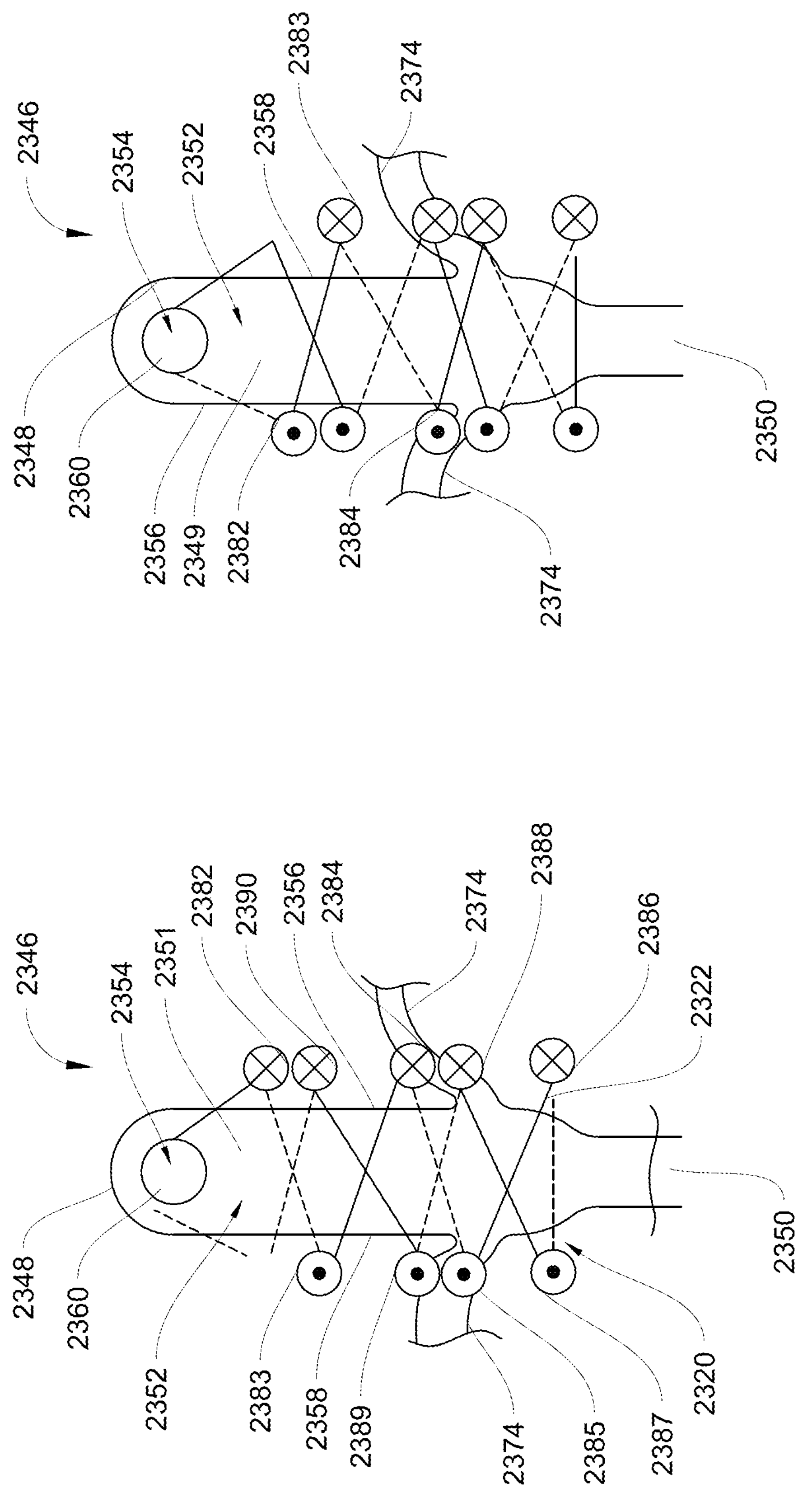
FIG. 23A is a flat schematic diagram of the commissural post of the frame and the suture pattern for attachment of the valve construct to the frame as viewed from the outer surface of the valve prosthesis, in accordance with at least one embodiment of the present disclosure.
FIG. 23B is a flat schematic diagram of the commissural post of the frame and the suture pattern shown in FIG. 23A but as viewed from the inner surface of the valve prosthesis.

The valve construct may be attached to the expandable frame in any of the embodiments shown in FIGS. 11-21, or in other similar embodiments, with a reduced number of sutures relative to other commercialized transcathether aortic valve devices. FIG. 22 shows a suture pattern on an expandable frame 2210 similar to the expandable frame shown at least in FIG. 12. Expandable frame 2210 may have a proximal end 2212 and a distal end 2214 opposite the proximal end 2212. The expandable frame may have a plurality of commissure posts 2246 at or substantially near the proximal end 2212. Each commissure post 2246 may have a proximal end 2248 and a distal end 2250. Each post 2246 may comprise at least one strut 2252 and at least one attachment feature 2254 connected to or embedded in the strut 2252. The at least one attachment feature 2254 may comprise a tab 2258 with at least one opening 2260 disposed within the tab 2258. The expandable frame further comprises cusp struts 2274 attached to either side of the post 2246. In embodiments where the valve construct is a single-piece valve construct, the attachment of the valve construct to an expandable frame 2210 may comprise a suturing pattern 2200 as shown in FIG. 22. The suturing pattern 2200 comprises three semi-circles 2220, each semi-circle 2220 corresponding to one leaflet of the valve construct. Each semi-circle 2220 comprises between 10 and 45 stitches 2221. In some embodiments, each semi-circle comprises between 20 and 30 stitches 2221. The suturing pattern 2200 may comprise one suture 2222 that has a first end 2223 and a second end 2225. In at least one embodiment, the first end 2223 and the second end 2225 are knotted together to complete the suturing pattern 2200. In some embodiments, the first end 2223 and the second end 2225 may be knotted at a strut of the frame. In other embodiments, the first end 2223 and the second end 2225 may be knotted around one of the posts 2254. In some embodiments, the suturing pattern 2200 consists only of a locking stitch.

commissure posts of the expandable frame according to FIGS. 23A and 23B. FIG. 23A shows one example of the commissure suture pattern 2320 from the vantage point of the outer surface of the expandable frame 2210, and FIG. 23B shows the suture pattern 2320 of FIG. 23A from the vantage point of the inner surface of the expandable frame 2210. In at least one embodiment the suture pattern 2320 comprises one suture 2322. The commissure post 2346 comprises a proximal end 2348 and a distal end 2350. The commissure post further comprises an inner surface 2349 and an outer surface 2351. The commissure post 2346 further comprises a strut 2352 and an attachment feature 2354. The strut 2352 has a first side 2356 and a second side 2358. Cusp struts 2374 extend from either side 2356, 2358 of the strut 2352. The attachment feature as shown comprises an opening 2360. In at least one embodiment, the commissure suture pattern 2320 comprises a suture 2322 with a first end 2380 and a second end 2381. The first end 2380 is disposed within the opening 2360 of the attachment feature 2354. The suture 2322 then extends from the first end 2380 over the outer surface 2351 of the commissure post 2346 to the first side 2356 to point 2382. At point 2382, the suture 2322 crosses over the inner surface 2349 of the commissure post 2346 to the second side 2358 to point 2383. At point 2383, the suture 2322 crosses back over the outer surface 2351 to the strut 2374 adjacent side 2356, in particular to the top of the strut 2374 to point 2384. At point 2384, the suture 2322 crosses over the inner surface 2349 to the bottom of the strut 2374 adjacent side 2358 to point 2385. At point 2385, the suture 2322 crosses over the outer surface 2351 towards a distal end of the commissure post 2346 at the first side 2358 to point 2386 and then crosses over the inner surface 2349 to point 2387. At point 2387, the suture 2322 crosses over the outer surface 2351 to the bottom of the strut 2374 adjacent side 2356 to point 2388. At point 2388, the suture 2322 crosses over the inner surface 2349 to the top of the strut 2374 adjacent side 2358 to point 2389. At point 2389, the suture 2322 then crosses over the outer surface 2351 to a point 2389 between point 2382 and point 2384. The suture 2322 then crosses over the inner surface 2389 to second end 2381 through the opening 2360. The first end 2380 and the second end 2381 can be connected to one another with a secured knot. In a preferred embodiment, when suturing the valve construct to the commissural post, the valve construct is positioned sufficiently close to the frame to ensure there is no post gap and also that the valve construct can adequately coapt under pressure.

Figure 24:
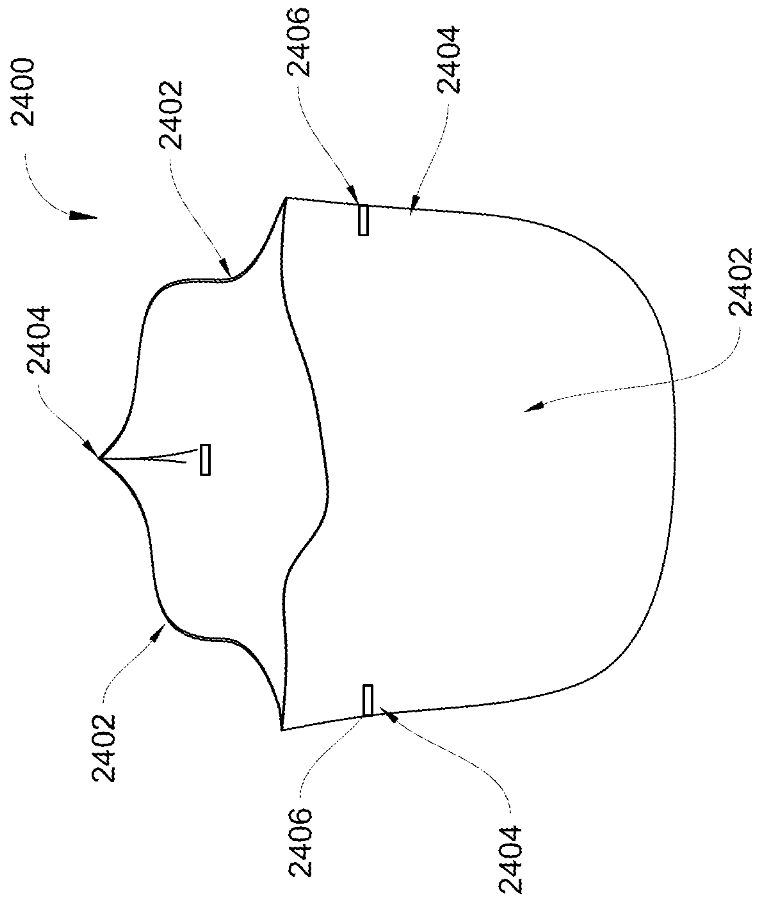
FIG. 24 is a perspective view of the valve construct that may be connected to the frame as shown in FIGS. 23A-23B.

In some embodiments, to facilitate attachment of the valve construct to the posts as described above with respect to FIGS. 23A and 23B, the valve construct may be modified to insert the post into a portion of the valve construct. One example is shown in FIG. 24. Valve construct 2400 is a single-piece valve construct with leaflets 2402 and commissural regions 2404 molded monolithically between adjacent leaflets. A slit 2406 may be cut into the valve construct 2400 at each commissural region 2404, and then the commissural post of the expandable frame can be inserted into the slit such that some of the valve construct 2400 is on the outer surface of the expandable frame (and more particularly the commissural post) once attached to the frame.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention.

What is claimed is:

1. A prosthetic heart valve having an inflow end at a distal end of the prosthetic heart valve and an outflow end at a proximal end of the prosthetic heart valve, the prosthetic heart valve configured to: (i) open to allow blood flow from the inflow end to the outflow end and (ii) close to prevent blood flow from the outflow end to the inflow end, the prosthetic heart valve comprising:

a stent frame that is reconfigurable between a low-profile delivery configuration and an expanded operable configuration in which the stent frame is cylindrical, the stent frame comprising:

an expandable region comprising multiple rows of cells including a first row of cells at the inflow end;

a cusp region comprising a row of cusp region cells at the outflow end, wherein a plurality of cusp struts define a proximal end of the row of cusp region cells; and a plurality of commissural posts, wherein a proximal portion of each commissural post extends proximally from a juncture of two cusp struts of the plurality of cusp struts; and a valve member material made of collagen-based biomaterial attached to the stent frame and comprising: (i) a plurality of U-shaped leaflets that are molded and cross-linked to retain a three-dimensional shape and (ii) commissural regions between adjacent U-shaped leaflets of the plurality of U-shaped leaflets, wherein the commissural regions of the valve member material are sutured directly to the proximal portion of each commissural post, and wherein an inflow end of the valve member material is defined by curved edges of the plurality of U-shaped leaflets that are sutured to the stent frame at the expandable region.

2. The prosthetic heart valve of claim 1, wherein the curved edges of the plurality of U-shaped leaflets are sutured to the stent frame using a suture pattern that corresponds to the curved edges of the plurality of U-shaped leaflets.

3. The prosthetic heart valve of claim 1, wherein the curved edges of the plurality of U-shaped leaflets comprise semi-circular shapes.

4. The prosthetic heart valve of claim 1, wherein the curved edges of the plurality of U-shaped leaflets are sutured to the stent frame using a U-shaped suture pattern that corresponds to the curved edges of the plurality of U-shaped leaflets.

5. The prosthetic heart valve of claim 1, wherein the valve member material consists of the plurality of U-shaped leaflets and the commissural regions.

6. The prosthetic heart valve of claim 5, wherein each commissural region defines a slit opening.

7. The prosthetic heart valve of claim 6, wherein each commissural post of the plurality of commissural posts defines an opening.

8. The prosthetic heart valve of claim 6, wherein each commissural post extends through the slit opening of one of the commissural regions.

9. The prosthetic heart valve of claim 8, wherein portions of the valve member material are disposed on an outer surface of the stent frame.

10. The prosthetic heart valve of claim 8, wherein portions of the valve member material are disposed on an outer surface of the proximal portion of each commissural post.

11. A prosthetic heart valve having an inflow end at a distal end of the prosthetic heart valve and an outflow end at a proximal end of the prosthetic heart valve, the prosthetic heart valve configured to: (i) open to allow blood flow from the inflow end to the outflow end and (ii) close to prevent blood flow from the outflow end to the inflow end, the prosthetic heart valve comprising:

a stent frame that is reconfigurable between a low-profile delivery configuration and an expanded operable configuration in which the stent frame is cylindrical, the stent frame comprising:

an expandable region comprising multiple rows of cells including a first row of cells at the inflow end;

a cusp region comprising a row of cusp region cells at the outflow end, wherein a plurality of cusp struts define a proximal end of the row of cusp region cells; and a plurality of commissural posts, wherein a proximal portion of each commissural post extends proximally from a juncture of two cusp struts of the plurality of cusp struts; and a valve member material attached to the stent frame and comprising: (i) a plurality of U-shaped leaflets and (ii) commissural regions between adjacent U-shaped leaflets of the plurality of U-shaped leaflets, wherein the commissural regions of the valve member material are sutured directly to the proximal portion of each commissural post, and wherein an inflow end of the valve member material is defined by curved edges of the plurality of U-shaped leaflets that are sutured to the stent frame at the expandable region.

12. The prosthetic heart valve of claim 11, wherein the curved edges of the plurality of U-shaped leaflets are sutured to the stent frame using a suture pattern that corresponds to the curved edges of the plurality of U-shaped leaflets.

13. The prosthetic heart valve of claim 11, wherein the curved edges of the plurality of U-shaped leaflets comprise semi-circular shapes.

14. The prosthetic heart valve of claim 11, wherein the curved edges of the plurality of U-shaped leaflets are sutured to the stent frame using a U-shaped suture pattern that corresponds to the curved edges of the plurality of U-shaped leaflets.

15. The prosthetic heart valve of claim 11, wherein the valve member material consists of the plurality of U-shaped leaflets and the commissural regions.

16. The prosthetic heart valve of claim 15, wherein each commissural region defines a slit opening.

17. The prosthetic heart valve of claim 16, wherein each commissural post of the plurality of commissural posts defines an opening.

18. The prosthetic heart valve of claim 16, wherein each commissural post extends through the slit opening of one of the commissural regions.

19. The prosthetic heart valve of claim 18, wherein portions of the valve member material are disposed on an outer surface of the stent frame.

20. The prosthetic heart valve of claim 18, wherein portions of the valve member material are disposed on an outer surface of the proximal portion of each commissural post.

* * * * *